(12) United States Patent
Roh et al.

(10) Patent No.: US 10,426,438 B2
(45) Date of Patent: Oct. 1, 2019

(54) ULTRASOUND APPARATUS AND METHOD OF MEASURING ULTRASOUND IMAGE

(71) Applicant: SAMSUNG MEDISON CO., LTD., Gangwon-do (KR)

(72) Inventors: Young-Tae Roh, Gangwon-do (KR); Duke-Man Hur, Gangwon-do (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 765 days.

(21) Appl. No.: 14/660,758

(22) Filed: Mar. 17, 2015

(65) Prior Publication Data
US 2015/0265247 A1    Sep. 24, 2015

(30) Foreign Application Priority Data
Mar. 18, 2014  (KR) .................. 10-2014-0031819

(51) Int. Cl.
*A61B 8/00* (2006.01)
*A61B 8/08* (2006.01)
*A61B 8/06* (2006.01)

(52) U.S. Cl.
CPC ............... *A61B 8/468* (2013.01); *A61B 8/08* (2013.01); *A61B 8/461* (2013.01); *A61B 8/463* (2013.01); *A61B 8/465* (2013.01); *A61B 8/467* (2013.01); *A61B 8/469* (2013.01); *A61B 8/485* (2013.01); *A61B 8/486* (2013.01); *A61B 8/488* (2013.01); *A61B 8/5207* (2013.01); *A61B 8/5223* (2013.01); *A61B 8/54* (2013.01); *A61B 8/06* (2013.01); *A61B 8/0891* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,315,999 A | * | 5/1994 | Kinicki | A61B 8/467 600/443 |
| 6,733,454 B1 | * | 5/2004 | Bakircioglu | A61B 8/06 600/453 |
| 8,951,200 B2 | | 2/2015 | Mo et al. | |

(Continued)

FOREIGN PATENT DOCUMENTS

| | | |
|---|---|---|
| CN | 102711626 A | 10/2012 |
| CN | 103455710 A | 2/2015 |

(Continued)

OTHER PUBLICATIONS

Extended European Search Report dated Aug. 25, 2015 issued in EP 15154812.0.

(Continued)

*Primary Examiner* — Bo Joseph Peng
(74) *Attorney, Agent, or Firm* — Morgan, Lewis & Bockius LLP

(57) ABSTRACT

Provided is a method of measuring an ultrasound image in an ultrasound apparatus. The method includes: displaying an ultrasound image on a screen; receiving a first user input of selecting at least one coordinate on the ultrasound image; determining a first measurement tool corresponding to the first user input based on a type of the first user input; and acquiring measurement information on the ultrasound image by using the determined first measurement tool.

31 Claims, 18 Drawing Sheets

(56) References Cited

U.S. PATENT DOCUMENTS

| | | | |
|---|---|---|---|
| 9,072,489 B2 | 7/2015 | Chono et al. | |
| 2007/0299342 A1* | 12/2007 | Hayasaka | A61B 8/00 600/443 |
| 2008/0208047 A1 | 8/2008 | Delso | |
| 2008/0228061 A1* | 9/2008 | Habets | G06F 3/0481 600/407 |
| 2009/0076384 A1* | 3/2009 | Saad | A61B 8/00 600/437 |
| 2012/0130223 A1* | 5/2012 | Reicher | G06F 19/321 600/407 |

FOREIGN PATENT DOCUMENTS

| | | | | |
|---|---|---|---|---|
| EP | 2522279 A1 | | 11/2012 | |
| EP | 2702947 A1 | * | 3/2014 | ............ A61B 8/467 |
| JP | 2005-270317 A | | 10/2005 | |
| JP | 2006-192030 A | | 7/2006 | |
| JP | 2007-097816 A | | 4/2007 | |
| JP | 2013-111434 A | | 6/2013 | |
| KR | 10-2009-0069788 A | | 7/2009 | |

OTHER PUBLICATIONS

Office Action issued in Chinese Application No. 201510119336.4 dated Jan. 22, 2019, with English translation.

\* cited by examiner

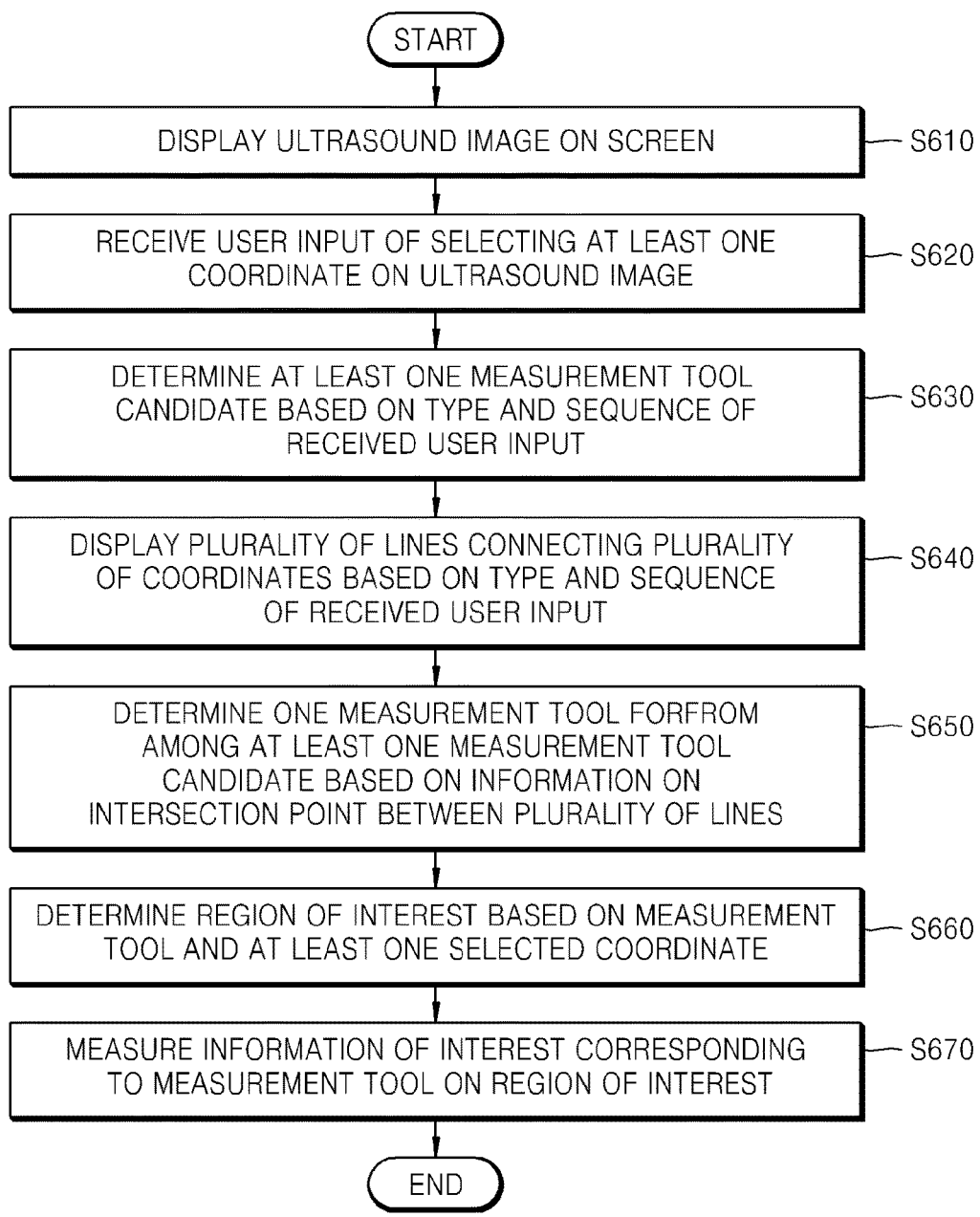

ULTRASOUND APPARATUS AND METHOD OF MEASURING ULTRASOUND IMAGE

RELATED APPLICATION

This application claims the benefit of Korean Patent Application No. 10-2014-0031819, filed on Mar. 18, 2014, in the Korean Intellectual Property Office, the disclosure of which is incorporated herein in its entirety by reference.

BACKGROUND

1. Field

One or more exemplary embodiments relate to an ultrasound apparatus and method that measure information of interest based on a user input.

2. Description of the Related Art

An ultrasound diagnosis apparatus transmits an ultrasound signal from a body surface of an object to a target region in the body and acquires an image of soft tissue tomography or blood flow by using information on an ultrasound signal reflected from tissue in the body.

The ultrasound diagnosis apparatus is small in size and inexpensive, and is capable of displaying an ultrasound image in real time. Furthermore, an ultrasound diagnosis apparatus is safe because an object is not exposed to X-ray radiation. Hence, an ultrasound diagnosis apparatus is widely used along with other image diagnosis apparatuses, such as an X-ray diagnosis apparatus, a computerized tomography (CT) scanner, a magnetic resonance imaging (MRI) machine, and a nuclear medicine diagnosis apparatus.

SUMMARY

One or more exemplary embodiments include an apparatus and method that determine a measurement tool according to a user input and measure an ultrasound image by using the determined measurement tool.

Additional aspects will be set forth in part in the description which follows and, in part, will be apparent from the description, or may be learned by practice of the presented exemplary embodiments.

According to one or more exemplary embodiments, a method of measuring an ultrasound image in an ultrasound apparatus includes: displaying an ultrasound image on a screen; receiving a first user input of selecting at least one coordinate on the ultrasound image; determining a first measurement tool corresponding to the first user input based on a type of the first user input; and acquiring measurement information on the ultrasound image by using the determined first measurement tool.

The type of the first user input may include at least one of a click, a double click, and a click and drag.

The determining of the first measurement tool may include determining the first measurement tool in consideration of a type of the ultrasound image.

The type of the ultrasound image may include at least one of a brightness (B) mode image, a motion (M) mode image, a spectral Doppler image, a color Doppler image, a tissue Doppler image, and an elastic Doppler image.

The determining of the first measurement tool may include: comparing the type of the first user input with preset input pattern information; and determining the first measurement tool corresponding to the first user input based on a result of the comparison.

The preset input pattern information may include at least one of input sequence information, input position information, click duration information, and drag direction information.

The determining of the first measurement tool corresponding to the first user input may include: displaying a plurality of lines by using the at least one coordinate as a reference according to the first user input; and determining the first measurement tool based on a number of intersecting points between the plurality of lines, positions of an the intersecting points, and an intersection angle.

The acquiring of the measurement information on the ultrasound image may include measuring at least one of lengths and slopes of the displayed plurality of lines.

The acquiring of the measurement information on the ultrasound image may include: determining a region of interest based on the at least one coordinate; and measuring at least one of an area and circumference of the region of interest.

The plurality of lines may include a plurality of straight lines, and the acquiring of the measurement information on the ultrasound image may include measuring an intersection angle between the plurality of straight lines.

The acquiring of the measurement information on the ultrasound image may include, when the ultrasound image is a spectral Doppler image, acquiring velocity information on the spectral Doppler image by using the determined first measurement tool.

The acquiring of the measurement information on the ultrasound image may include: when the ultrasound image is a spectral Doppler image, selecting a partial time interval on the spectral Doppler image based on the at least one coordinate; and measuring at least one of a distance which blood moves or a distance which tissue moves over the partial time interval and an envelope of a spectral waveform on the spectral Doppler image.

According to one or more exemplary embodiments, an ultrasound apparatus includes: a display unit that displays an ultrasound image on a screen; a user input unit that receives a first user input of selecting at least one coordinate on the ultrasound image; and a control unit that determines a first measurement tool corresponding to the first user input based on a type of the first user input and acquires measurement information on the ultrasound image by using the determined first measurement tool.

The control unit may determine the first measurement tool in consideration of a type of the ultrasound image.

The control unit may compare the type of the first user input with preset input pattern information and determine the first measurement tool corresponding to the first user input based on a result of the comparison.

The control unit may display a plurality of lines by using the at least one coordinate as a reference according to the first user input; and determine the first measurement tool based on a number of intersecting points between the plurality of lines, positions of the intersecting points, and an intersection angle.

The control unit may measure at least one of lengths and slopes of the displayed plurality of lines.

The control unit may determine a region of interest based on at least one coordinate and measure at least one of an area and circumference of the region of interest.

The plurality of lines may include a plurality of straight lines, and the control unit may measure an intersection angle between the plurality of lines.

The control unit may acquire, when the ultrasound image is a spectral Doppler image, velocity information on the spectral Doppler image by using the determined first measurement tool.

The control unit may select, when the ultrasound image is a spectral Doppler image, a partial time interval on the spectral Doppler image based on the at least one coordinate, and measure at least one of a distance which blood moves or a distance which tissue moves over the partial time interval and an envelope of a spectral waveform on the spectral Doppler image.

BRIEF DESCRIPTION OF THE DRAWINGS

These and/or other aspects will become apparent and more readily appreciated from the following description of the exemplary embodiments, taken in conjunction with the accompanying drawings in which:

FIG. 6 is a flowchart of a method of determining a measurement tool based on a coordinate selected by a user in an ultrasound apparatus, according to an exemplary embodiment;

DETAILED DESCRIPTION

Figure 1B:
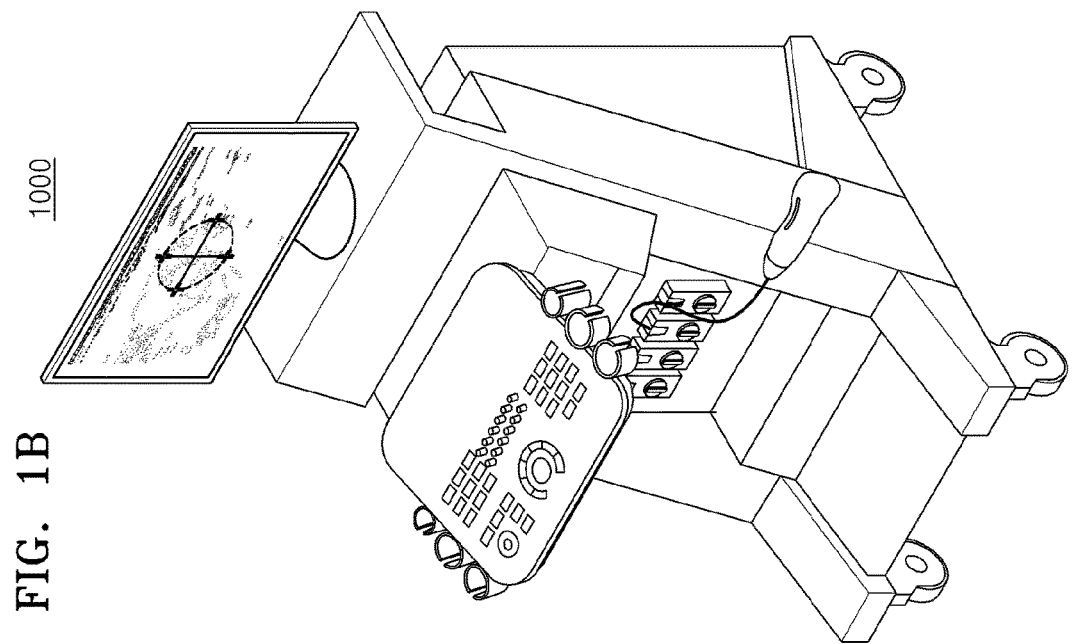
FIGS. 1A and 1B are diagrams illustrating a general ultrasound apparatus and an ultrasound apparatus according to an exemplary embodiment.

As the terms used herein, so far as possible, widely-used general terms are selected in consideration of functions in the exemplary embodiments; however, these terms may vary according to the intentions of those skilled in the art, the precedents, or the appearance of new technology. Also, in some cases, there may be terms that are optionally selected by the applicant, and the meanings thereof will be described in detail in the corresponding portions of the description of the exemplary embodiments. Therefore, the terms used herein are not simple terms and should be defined based on the meanings thereof and the overall description of the exemplary embodiments.

It will be understood that the terms "comprise", "include", and "have", when used herein, specify the presence of stated elements, but do not preclude the presence or addition of other elements, unless otherwise defined. Also, the terms "unit" and "module" used herein represent a unit for processing at least one function or operation, which may be implemented by hardware, software, or a combination of hardware and software.

Throughout the specification, the term "ultrasound image" refers to an image of an object, which is acquired by using ultrasound waves. The term "object" may refer to a part of a body. For example, the object may be an organ, such as a liver, a heart, a nuchal translucency (NT), a brain, a breast, or an abdomen, or a fetus.

The ultrasound image may be variously implemented. For example, the ultrasound image may be at least one of a brightness mode (B mode) image that shows a magnitude of an ultrasound echo signal reflected from an object by brightness, a color mode (C mode) image that shows a velocity of a moving object by colors by using the Doppler effect, a Doppler mode (D mode) image that shows an image of a moving object in a spectrum form by using the Doppler effect, a motion mode (M mode) image that shows movement of an object with time at a specific position, and an elastic mode image that shows a reaction difference between a state in which compression is applied to an object and a state in which the compression is not applied to the object, but is not limited thereto. According to an exemplary embodiment, the ultrasound image may be a two-dimensional image, a three-dimensional image, or a four-dimensional image.

In addition, throughout the specification, the term "user" may refer to a medical expert, such as a doctor, a nurse, a medical laboratory technologist, or sonographer, but is not limited thereto.

Exemplary embodiments will be described below in detail with reference to the accompanying drawings so that those of ordinary skill in the art may easily implement the exemplary embodiments. The exemplary embodiments may, however, have different forms and should not be construed as being limited to the descriptions set forth herein. In addition, portions irrelevant to the description of the exemplary embodiments will be omitted in the drawings for a clear description of the exemplary embodiments, and like reference numerals will denote like elements throughout the specification.

Figure 1A:
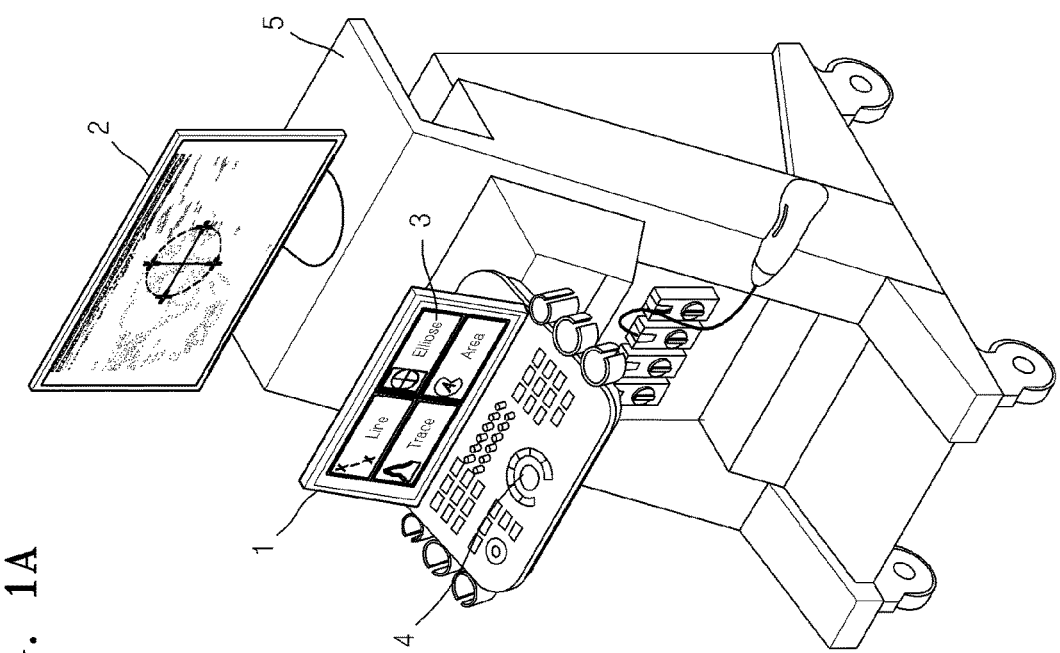

FIGS. 1A and 1B are diagrams illustrating a general ultrasound apparatus and an ultrasound apparatus according to an exemplary embodiment.

Referring to FIG. 1A, a user sets a region of interest on an ultrasound image and measures information of interest corresponding to the region of interest so as to acquire information on an object from the ultrasound image. In this case, the user may set the region of interest by using a user interface provided by the general ultrasound apparatus 5, and measure the information of interest.

For example, the user may select an oval measurement interface 3. The oval measurement interface 3 may be a user interface configured to set an oval region on the ultrasound image displayed on a display unit 2 and to measure an area of the set oval region. After the oval measurement interface 3 is selected, the user selects coordinates for setting the oval region on the ultrasound image by using the oval measurement interface 3. In the general ultrasound apparatus 5, the user may perform both the operation of selecting the user interface and the operation of setting the region of interest so as to measure the information of interest.

On the other hand, the general ultrasound apparatus 5 may include a trackball 4 provided with a control panel as an input tool for selecting a coordinate. In this case, the user touches a touchscreen 1 to select a measurement tool, and moves an arm, and manipulates the trackball 4 to set the region of interest, thereby forcing the user to move the arm continuously. The user is easily fatigued due to such repeated arm movements.

Referring to FIG. 1B, when the user selects the coordinates for setting the region of interest, the ultrasound apparatus 1000 according to the exemplary embodiment may measure information of interest which the user desires to be measured based on the selected coordinates.

The ultrasound apparatus 1000 according to the exemplary embodiment may determine a measurement tool based on a user input of selecting a coordinate. In addition, the ultrasound apparatus 1000 according to the exemplary embodiment may measure information of interest on the region of interest selected on the ultrasound image based on the determined measurement tool.

Therefore, when the user selects coordinates for setting a region of interest, the ultrasound apparatus 1000 according to the exemplary embodiment may measure information of interest which the user desires to be measured on the ultrasound image based on the selected coordinates although the user selects no user interface.

A method of measuring information of interest on a region of interest on the ultrasound image in the ultrasound apparatus 1000 will be described below with reference to FIG. 2 in detail.

Figure 2:
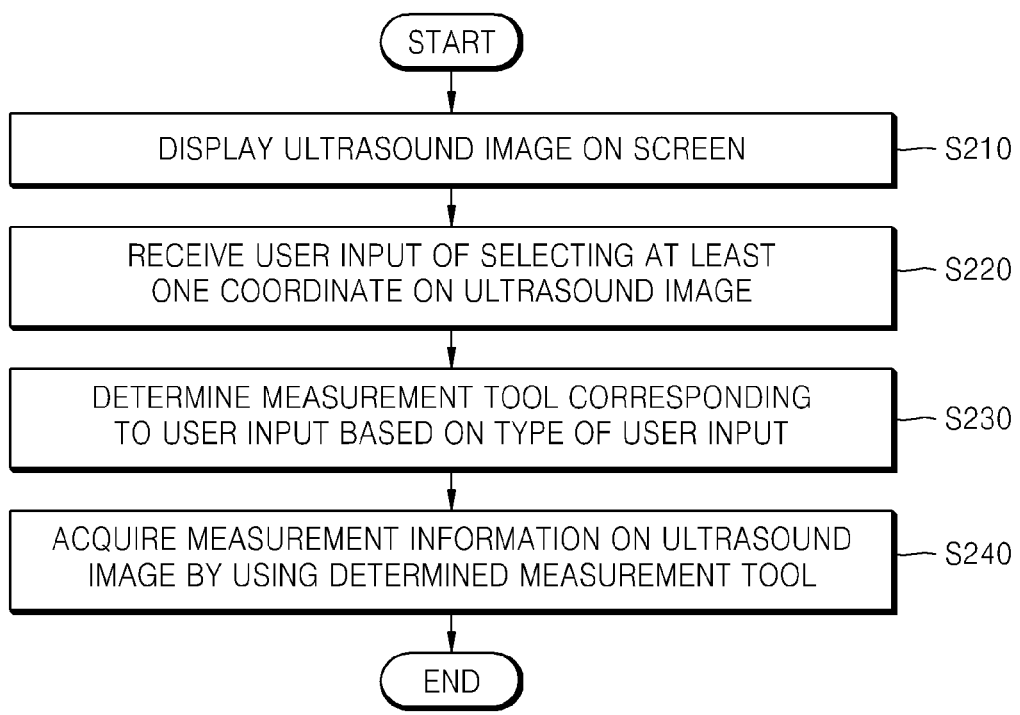
FIG. 2 is a flowchart of a method of selecting a measurement tool in an ultrasound apparatus according to an exemplary embodiment.

FIG. 2 is a flowchart of a method of selecting a measurement tool in the ultrasound apparatus 1000 according to an exemplary embodiment.

In operation S210, the ultrasound apparatus 1000 may display an ultrasound image on a screen.

In some exemplary embodiments, the ultrasound image may be an image acquired by directly capturing an object by using the ultrasound apparatus 1000. In some exemplary embodiments, the ultrasound image may include an ultrasound image received from an external apparatus.

In some exemplary embodiments, the ultrasound image may be at least one of a brightness (B) mode image, a motion (M) mode image, a spectral Doppler image, a color Doppler image, a tissue Doppler image and an elastic Doppler image, but is not limited thereto.

In operation S220, the ultrasound apparatus 1000 may receive a user input of selecting at least one coordinate on the ultrasound image.

In some exemplary embodiments, the user input may be received through a physical input device included in the ultrasound apparatus 1000.

For example, the user input may be received through a trackball provided with a control panel of the ultrasound apparatus 1000.

For example, the user input may be received through a touchpad or a touchscreen connected to the ultrasound apparatus 1000. The ultrasound apparatus 1000 may receive a user input via the touchscreen on which the ultrasound image is displayed. The ultrasound apparatus 1000 may receive the user input through a separate touchpad or touchscreen provided with the ultrasound apparatus 1000 rather than the touchscreen on which the ultrasound image is displayed.

As the user moves the input device provided with the ultrasound apparatus 1000, the ultrasound apparatus 1000 according to the exemplary embodiment may display an image (for example, a cursor) representing a position on the screen indicated by the input device on the screen of the ultrasound apparatus.

The user may select at least one position on the ultrasound image in consideration of the image representing the position of the input device, which is displayed on the screen. As the user selects at least one position on the ultrasound image displayed on the screen of the ultrasound apparatus 1000, the ultrasound apparatus 1000 may determine a coordinate corresponding to the selected position.

In operation S230, the ultrasound apparatus 1000 may determine a measurement tool corresponding to the user input based on a type of the user input.

In some exemplary embodiments, the type of the user input may include a click, a double click, and a click and drag, but is not limited thereto.

The click may refer to an operation performed by a user to position a cursor at a desired coordinate using an input tool (for example, a mouse or a trackball), in which the user presses a position selection button, and then releases the button from a pressed state. In some exemplary embodiments, the click may be referred to as a single click.

The double click may refer to an operation performed by a user to position a cursor at a desired coordinate using an input tool, in which the user clicks twice in rapid succession (for example, within 0.5 second). In some exemplary embodiments, the double click may be referred to as a double set.

The click and drag may refer to an operation performed by a user to position a cursor at a desired coordinate using an input tool, in which the user moves the input tool a certain distance in a state in which the position selection button is pressed, and then releases the position selection button from the pressed state. In some exemplary embodiments, the click and drag may be referred to as a single drag.

In some exemplary embodiments, the measurement tool may refer to a tool for measuring information of interest on a region of interest.

In some exemplary embodiments, the region of interest may refer to a region on the ultrasound image, which the user desires to be measured. For example, the region of interest may include a line segment connecting two coordinates, a circular region, an oval region, a specific angle, and a specific time interval, but is not limited thereto.

In some exemplary embodiments, information of interest may refer to information which the user desires to be measured on the ultrasound image. For example, the information of interest may include a length, an angle, a magnitude, an area, a velocity, a movement distance, and the form of waveform, but it not limited thereto.

In some exemplary embodiments, the measurement tool may include a tool for measuring a length of a line segment of interest, a tool for measuring a slope of a line segment of interest, a tool for measuring an angle at an intersection point of interest, a tool for measuring a circumference of a region of interest, a tool for measuring a feature value of a graph associated with a region of interest, a tool for measuring an integral value of a graph associated with a region of interest, a tool for measuring a slope of a graph associated with a region of interest, and a tool for measuring a time interval on a graph, but is limited thereto.

In some exemplary embodiments, determining a measurement tool may refer to determining information of interest which the user desires to be measured and a shape of a region of interest in which the information of interest is to be measured.

The ultrasound apparatus 1000 according to the exemplary embodiment may determine a measurement tool corresponding to a user input based on a result of comparing a type of the user input with preset input pattern information.

In some exemplary embodiments, the preset input pattern information may include at least one of input sequence information, input position information, click duration information, and drag direction information, but is not limited thereto.

In the ultrasound apparatus 1000, pieces of input pattern information may be set corresponding to a plurality of measurement tools, respectively. That is, the measurement tool may be stored in a state of being mapped to input pattern information.

When an input of selecting at least one coordinate is received from the user, the ultrasound apparatus 1000 may analyze a user input pattern, and extract an input pattern corresponding to the analyzed user input pattern. The ultrasound apparatus 1000 may determine a measurement tool corresponding to the extracted input pattern.

The ultrasound apparatus 1000 according to the exemplary embodiment may determine the measurement tool in consideration of a type of the ultrasound image.

When user inputs of selecting two coordinates on a B mode image are received, the ultrasound apparatus 1000 may determine a measurement tool for measuring a length of a straight line. When user inputs of selecting two coordinates on a Doppler image is received, the ultrasound apparatus 1000 may determine a measurement tool for measuring a ratio of velocities corresponding to the selected coordinates on the object.

On the other hand, a shape of the region of interest may be previously determined according to a measurement tool. For example, an intersection point is necessary to measure an angle. In addition, two circles which do not intersect are necessary to compare a diameter of a stenosis area with a diameter of a normal blood vessel. A closed curve and at least one straight line intersecting the closed curve are necessary to measure a volume of a heart using the rule of disks. That is, each of specific measurement tools may have a predetermined shape for a region of interest, corresponding to the measurement tool. Therefore, a predetermined shape of a region of interest may be generated corresponding to a measurement tool based on a coordinate selected by a user input such that a specific measurement tool is selected. Therefore, a selected coordinate may also be a condition for determining a measurement tool, in addition to a type and sequence of a user input.

The ultrasound apparatus 1000 according to the exemplary embodiment may determine a measurement tool based on a plurality of coordinates selected by a user input.

The ultrasound apparatus 1000 according to the exemplary embodiment may not only compare a type and sequence of a user input with preset user input pattern information, but consider the plurality of selected coordinates to determine a measurement tool. That is, a condition which a selected coordinate is required to satisfy may be further set corresponding to a measurement tool in the ultrasound apparatus 1000, in addition to the preset user input pattern information.

For example, when a plurality of lines are generated by connecting a plurality of selected coordinates, a relationship between the plurality of lines, which the plurality of lines need to satisfy may be set corresponding to a measurement tool.

In some exemplary embodiments, the plurality of lines may include a straight line and a curved line, but are not limited thereto.

The relationship between the plurality of lines may refer to information on relative positions of coordinates which the coordinates need to satisfy so as to generate a shape of a region of interest expected according to a measurement tool. In addition, the relationship between the plurality of lines may include at least one of the number of intersection points between the plurality of lines, a position of an intersection point, and an intersection angle.

The method of generating a plurality of lines by connecting the plurality of selected coordinates may be previously set according to type and sequence of a user input. For example, when user inputs of respectively clicking two coordinates are received, a method of generating one line segment which is previously set and corresponds to the user inputs of respectively clicking two coordinates may be implemented.

Therefore, the ultrasound apparatus 1000 may compare the types and sequence of user inputs with preset input pattern information and select at least one measurement tool candidate. In addition, the ultrasound apparatus 1000 may generate a plurality of lines corresponding to the types and sequence of the user inputs. The ultrasound apparatus may determine whether the plurality of generated lines satisfy an intersection-point condition of the at least one selected measurement tool candidate. When there is an intersection-point condition which the plurality of generated lines satisfy among intersection-point conditions of the at least one measurement tool candidate, the ultrasound apparatus 1000 may determine a measurement tool that satisfies the intersection-point condition as a measurement tool.

In operation S240, the ultrasound apparatus 1000 may acquire measurement information on the ultrasound image by using the determined measurement tool.

In the ultrasound apparatus 1000 according to the exemplary embodiment, information of interest to be measured may be previously set corresponding to the measurement tool. For example, a measurement tool for measuring an angle may be set to measure an angle between two line segments.

In the ultrasound apparatus 1000 according to the exemplary embodiment, a method of determining a region of interest may be previously set, corresponding to a measurement tool. For example, a method of generating a major axis and a minor axis based on the selected coordinate and determining an oval based on the generated major and minor axes may be set corresponding to the measurement tool for measuring an oval. For example, a method of generating an open curve based on selected coordinates and determining a closed curve based on the generated open curve may be set corresponding to a measurement tool for measuring an area of a closed curve.

The ultrasound apparatus 1000 according to the exemplary embodiment may store a method of measuring information of interest on a region of interest, corresponding to a measurement tool. For example, a measurement tool for measuring an angle may calculate a graph between two line segments and calculate an angle between the two line segments based on the calculated graph between the two line segments. A measurement tool for measuring a volume may cut an area of a closed curve into N slices of uniform thickness to generate N disks and add up volumes of the generated N disks to measure the entire volume of the closed curve.

The measurement information may refer to information about a result acquired by measuring information of interest. For example, the measurement information may refer to a measured length, a measured area, a measured volume, a measured velocity and a measured distance.

The ultrasound apparatus 1000 according to the exemplary embodiment may cancel a previous user input of selecting a coordinate on the ultrasound image.

For example, the ultrasound apparatus 1000 may receive a user input of cancelling the previous user input of selecting the coordinate on the ultrasound image. A user input pattern for cancelling a previous user input of selecting a coordinate on the ultrasound image may be previously set in the ultrasound apparatus 1000. Therefore, the ultrasound apparatus 1000 may compare an input pattern of the received user input with the previously set input pattern for cancelling a previous user input of selecting a coordinate on the ultrasound image. When the input pattern of the received user input is the same as the previously set input pattern for cancelling a previous user input of selecting a coordinate on the ultrasound image, the ultrasound apparatus 1000 may cancel a most recently received user input of a series of user inputs of selecting coordinates. When the most recently received user input is deleted, the ultrasound apparatus 1000 may switch to using a measurement tool determined in advance before the deleted user input is received.

For example, the ultrasound apparatus 1000 may receive a first user input and determine a first measurement tool based on the received first user input. The ultrasound apparatus 1000 may further receive a second user input and switch from using the first measurement tool to using a second measurement tool based on the received second user input and the first user input. In this case, the ultrasound apparatus 1000 may receive a user input of cancelling the previous user input of selecting the coordinate on the ultrasound image. When the user input of cancelling the previous user input of selecting the coordinate on the ultrasound image is received, the ultrasound apparatus 1000 may cancel the second user input that is a most recently received input. In addition, the ultrasound apparatus 1000 may cancel the determination of the second measurement tool and switch from using the second measurement tool to using the first measurement tool.

The ultrasound apparatus 1000 according to the exemplary embodiment may cancel all previous user inputs of selecting coordinates on the ultrasound image.

For example, the ultrasound apparatus 1000 may receive a user input of cancelling all previous user inputs of selecting coordinates on the ultrasound image. A user input pattern for cancelling all previous user inputs of selecting coordinates on the ultrasound image may be previously set in the ultrasound apparatus 1000. Therefore, the ultrasound apparatus 1000 may compare an input pattern of a received user input with the previously set input pattern for cancelling all previous user inputs of selecting coordinates on the ultrasound image. When the input pattern of the received user input is the same as the previously set input pattern for cancelling all previous user inputs of selecting coordinates on the ultrasound image, the ultrasound apparatus 1000 may cancel all of a series of user inputs of selecting coordinates. When the series of user inputs of selecting coordinates are all cancelled, the ultrasound apparatus 1000 may cancel a measurement tool which was determined based on the series of user inputs of selecting coordinates.

For example, the ultrasound apparatus 1000 may receive a first user input and determine a first measurement tool based on the received first user input. The ultrasound apparatus 1000 may further receive a second user input and a third user input and switch from using the first measurement tool to using a third measurement tool based on the received first to third user inputs. In this case, the ultrasound apparatus 1000 may receive a user input of cancelling all the previous user inputs of selecting coordinates on the ultrasound image. When the user input of cancelling all of the previous user inputs of selecting coordinates on the ultrasound image is received, the ultrasound apparatus 1000 may cancel all of the first to third user inputs. In addition, the ultrasound apparatus 1000 may cancel the determination of both the first measurement tool and the third measurement tool.

The ultrasound apparatus 1000 may provide a restore function and a reset function with respect to a user input of selecting coordinates on the ultrasound image.

Figure 3:
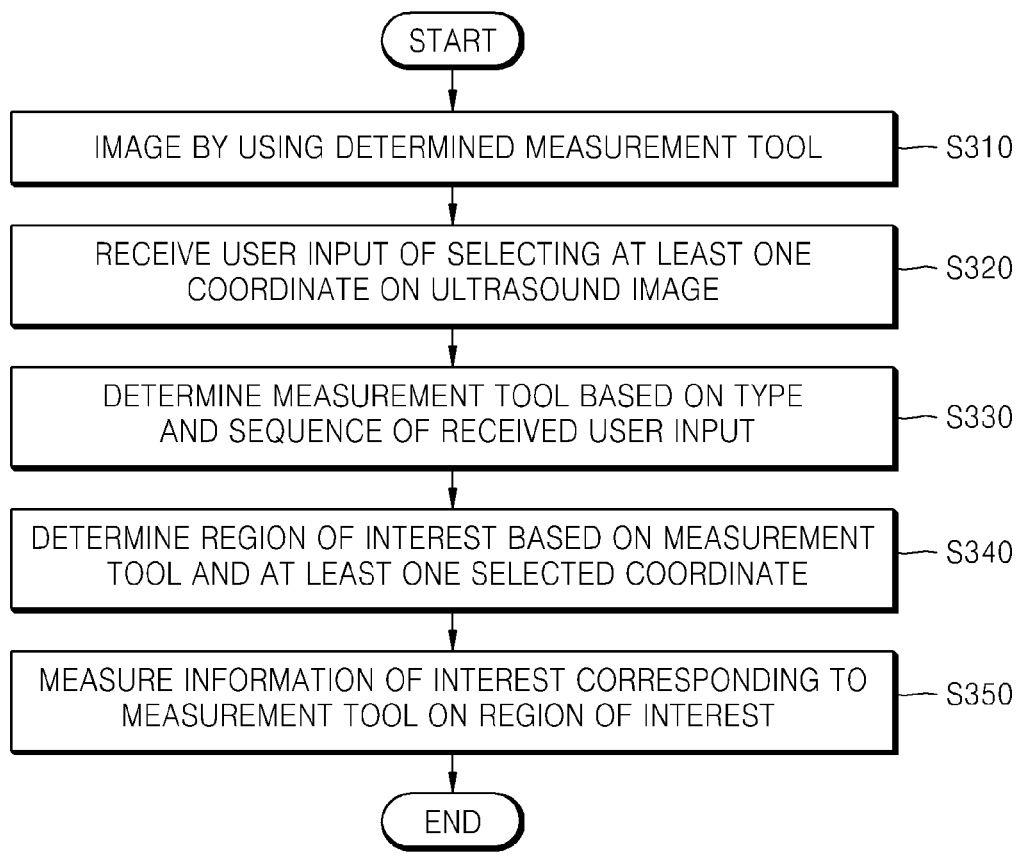
FIG. 3 is a flowchart of a method of determining a measurement tool based on a type and sequence of a user input in an ultrasound apparatus, according to an exemplary embodiment.

FIG. 3 is a flowchart of a method of determining a measurement tool based on a type and sequence of a user input in the ultrasound apparatus 1000, according to an exemplary embodiment.

In operation S310, the ultrasound apparatus 1000 may display an ultrasound image on a screen. In operation S320, the ultrasound apparatus 1000 may receive a user input of selecting at least one coordinate on the ultrasound image.

In operation S330, the ultrasound apparatus 1000 may determine a measurement tool based on a type and a sequence of the received user input.

The ultrasound apparatus 1000 according to the exemplary embodiment may compare the type and sequence of the received user input with preset input pattern information and determine the measurement tool to use.

When an input of selecting at least one coordinate is received from the user, the ultrasound apparatus 1000 may analyze a type and sequence of the user input, and extract an input pattern corresponding to the analyzed type and sequence of the user input. The ultrasound apparatus 1000 may determine a measurement tool corresponding to the extracted input pattern.

For example, the ultrasound apparatus 1000 may receive user inputs in a sequence of a double click, a click, and a click. Therefore, the ultrasound apparatus 1000 may determine the double click, the click, and the click as types of the user inputs. In addition, the ultrasound apparatus 1000 may determine that the double click is first performed, followed by two clicks. When a measurement tool for measuring an angle is set as a measurement tool mapped to an input pattern of the double click, the click, and the click, the ultrasound apparatus 1000 may determine the measurement tool for measuring an angle as a measurement tool corresponding to the types and sequence of the received user inputs.

In operation S340, the ultrasound apparatus 1000 may determine a region of interest based on the determined measurement tool and the at least one selected coordinate.

In the ultrasound apparatus 1000 according to the exemplary embodiment, a method of determining a region of interest may be previously set corresponding to a measurement tool. For example, a method of generating a major axis and a minor axis based on the selected coordinate and determining an oval based on the generated major and minor axes may be set corresponding to the measurement tool for measuring an oval.

The ultrasound apparatus 1000 may select a method of setting a region of interest corresponding to the determined measurement tool from a memory. The ultrasound apparatus 1000 may determine a region of interest by using the selected coordinate as a reference based on the selected method of setting a region of interest.

In operation S350, the ultrasound apparatus 1000 may measure information of interest corresponding to the determined measurement tool from the determined region of interest.

In the ultrasound apparatus 1000 according to the exemplary embodiment, information of interest to be measured may be previously set corresponding to a measurement tool. For example, the measurement tool for measuring an oval may be set to measure the circumference and area of an oval.

The ultrasound apparatus 1000 according to the exemplary embodiment may store a method of measuring information from a region of interest, corresponding to the measurement tool. For example, a measurement tool for measuring an angle may calculate a graph between two line segments and calculate an angle between the two line segments based on the calculated graph of the two line segments.

The ultrasound apparatus 1000 may select a method of measuring information of interest corresponding to the determined measurement tool from the memory. The ultrasound apparatus may measure information of interest from the region of interest on the ultrasound image, determined in operation S340 based on the selected method of measuring information of interest.

Figure 4B:
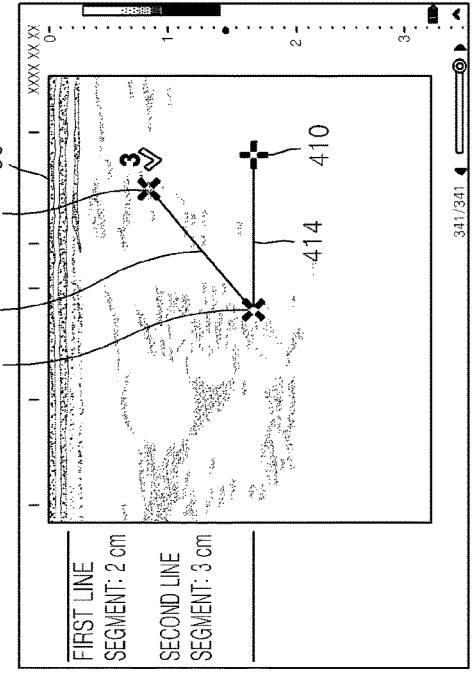
FIGS. 4A to 4C are diagrams illustrating an example in which an ultrasound apparatus measures an angle based on a user input, according to an exemplary embodiment.
Figure 4A:
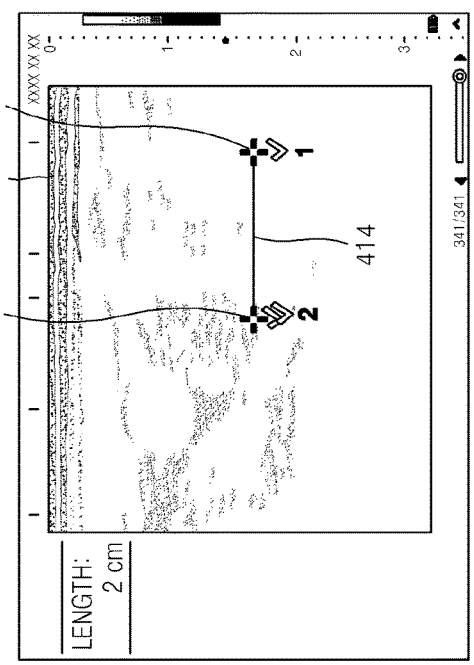
Figure 4C:
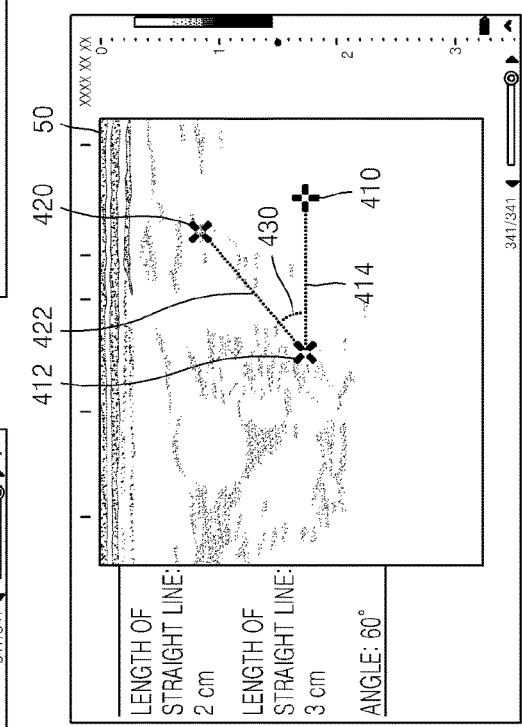

FIGS. 4A to 4C are diagrams illustrating an example in which the ultrasound apparatus 1000 according to an exemplary embodiment measures an angle based on a user input.

Referring to FIG. 4A, the ultrasound apparatus 1000 may display an ultrasound image 50 on a screen of the ultrasound apparatus 1000. The ultrasound image may include at least one of a B mode image, a C mode image, and a Doppler mode image, but is not limited thereto.

The ultrasound apparatus 1000 may determine a measurement tool based on a type and sequence of the received user input.

For example, the ultrasound apparatus 1000 may receive a user input of clicking a first coordinate 410 and a user input of double clicking a second coordinate 412. In the ultrasound apparatus 1000, a measurement tool for measuring a length may be set as a measurement tool corresponding to a user input pattern where the type of the first user input is a click and the type of the second user input is a double click.

Therefore, the ultrasound apparatus 1000 may select the measurement tool for measuring a length corresponding to the received user inputs from the memory. In addition, the ultrasound apparatus 1000 may calculate a length from the first coordinate 410 to the second coordinate 412. The ultrasound apparatus 1000 may display a line segment 414 connecting the first coordinate 410 and the second coordinate 412 to represent the region of interest. In addition, the ultrasound apparatus 1000 may display the measured length on the screen.

Referring to FIG. 4B, when the user clicks a third coordinate 420 in the state in which the first coordinate 410 and the second coordinate 412 are selected, the ultrasound apparatus 1000 may select the measurement tool for measuring a length as in the exemplary embodiment as illustrated in FIG. 4A and measure the length of a line segment connecting the second coordinate 412 and the third coordinate 420. In this case, the ultrasound apparatus 1000 may determine the line segment connecting the first coordinate 410 and the second coordinate 412 as a first line segment 414, and the line segment connecting the second coordinate 412 and the third coordinate 420 as a second line segment 422, and display the first line segment 414 and the second line segment 422 on the screen. The ultrasound apparatus 1000 may measure lengths of the first and second line segments 414 and 422 and displays the lengths.

In the ultrasound apparatus 1000, a measurement tool for measuring an angle may be set as a measurement tool corresponding to the types and sequence of user inputs, where the type of the first user input is a click, the type of the second user input is a double click, and the type of the third user input is a click. Therefore, the ultrasound apparatus 1000 may determine the measurement tool for measuring an angle as a measurement tool corresponding to the received user inputs.

In the ultrasound apparatus 1000, a method of generating two line segments by connecting selected coordinates in sequence, calculating a graph of the two generated line segments, and measuring an angle between the two line segments based on the calculated graph may be previously set as a method of measuring an angle corresponding to the measurement tool for measuring an angle. Therefore, the ultrasound apparatus 1000 may calculate the graph between the first line segment 414 and the second line segment 422. In addition, as illustrated in FIG. 4C, the ultrasound apparatus 1000 may calculate an intersection point between the first line segment 414 and the second line segment 422 and measure an angle between the two line segments at the calculated intersection point. The ultrasound apparatus 1000 may display the measured angle on the screen.

Although the user merely inputs coordinates for selecting an apex at which an angle is to be measured, without selecting a tool for measuring an angle, the ultrasound apparatus 1000 may measure and provide the angle at the apex which the user desires to be measured.

Figure 5B:
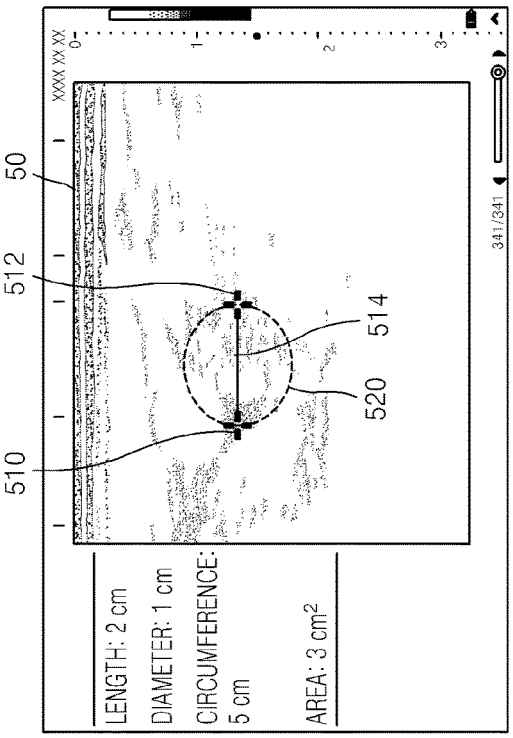
FIGS. 5A to 5C are diagrams illustrating an example in which an ultrasound apparatus measures an oval based on a user input, according to an exemplary embodiment.
Figure 5A:
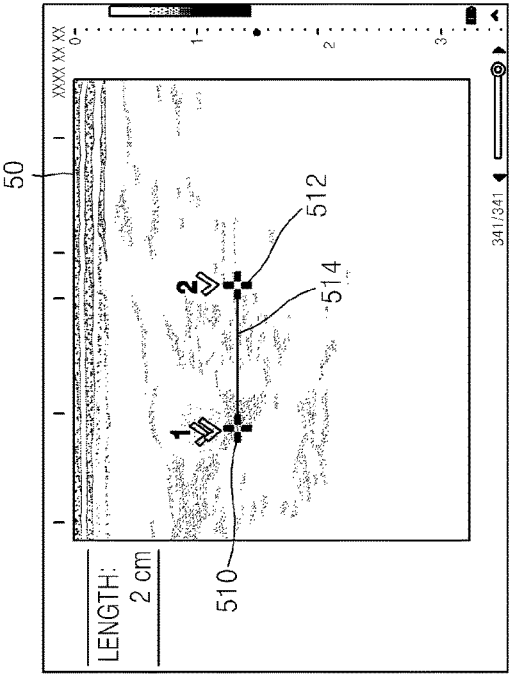
Figure 5C:
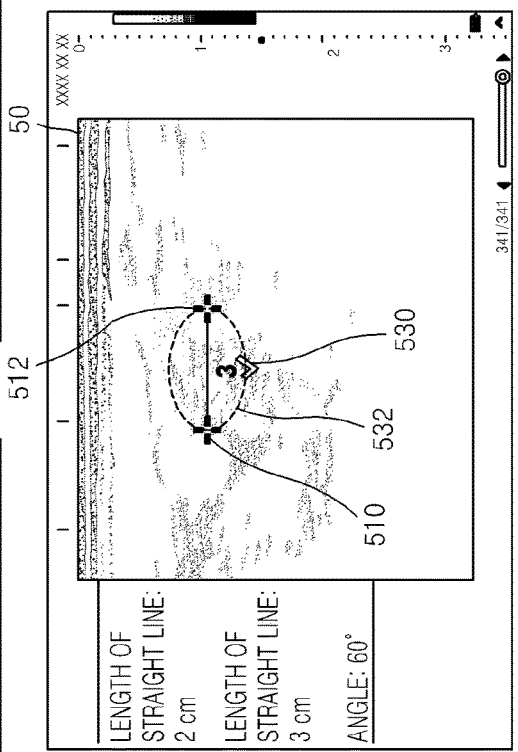

FIGS. 5A to 5C are diagrams illustrating an example in which the ultrasound apparatus 1000 according to an exemplary embodiment measures an oval based on a user input.

The ultrasound apparatus 1000 may determine a measurement tool based on a type and sequence of a received user input. The ultrasound apparatus 1000 may determine a plurality of measurement tools based on a type and sequence of the received user input. A plurality of measurement tools may be mapped to a type and sequence of one user input. The ultrasound apparatus 1000 may determine a plurality of measurement tools even when one input pattern is received from a user.

Referring to FIG. 5A, the ultrasound apparatus 1000 may receive user inputs of double clicking a first coordinate 510 and then clicking a second coordinate 512. In this case, the ultrasound apparatus 1000 may calculate a length of a line segment 514 connecting a first coordinate 510 and a second coordinate 512 as in the exemplary embodiment illustrated in FIG. 4A.

Referring to FIG. 5B, when user inputs of double clicking a first coordinate 510 and then clicking a second coordinate 512 are received, the ultrasound apparatus 1000 may determine a measurement tool for measuring an area and circumference of a circle.

The ultrasound apparatus 1000 may select, as a region of interest, a region defined by a circle 520 having a diameter which is equal to the length of a line segment 514 connecting the first coordinate 510 and the second coordinate 512. In addition, the ultrasound apparatus 1000 may measure the area of the circle 520 and the circumference of the circle 520 for information of interest.

In addition, the ultrasound apparatus 1000 may switch to using a different measurement tool when a user input of selecting a coordinate is received. For example, the ultrasound apparatus 1000 may determine a measurement tool for measuring the area and circumference of a circle based on a first input and a second input and measure the area and circumference of the circle as in the exemplary embodiment illustrated in FIG. 4B. Thereafter, when a third input is received as illustrated in FIG. 5C, the ultrasound apparatus 1000 may determine a measurement tool for measuring the area and circumference of an oval.

When a user input is received in which the user clicks a third coordinate 530 in the state in which the first coordinate 510 and the second coordinate 512 are selected, the ultrasound apparatus 1000 may select a measurement tool for measuring an oval as a measurement tool based on an input pattern of the received user input in which the type of the first input is a double click, the type of the second input is a click, and the type of the third input is a click.

Therefore, the ultrasound apparatus 1000 may determine a region of an oval 532 of which the major axis is a line segment connecting the first coordinate 510 and the second coordinate 512 and the minor axis is a line segment having a length of two times a vertical distance between the third coordinate 530 and the line segment 514 as a region of interest. In addition, the ultrasound apparatus 1000 may measure the circumference of the oval 532 and the area of the oval 532 as information of interest. In addition, the ultrasound apparatus 1000 may display the shape of the oval 532, the measured circumference of the oval 532 and the measured area of the oval 532 on the screen of the ultrasound apparatus 1000.

Although the user merely selects coordinates for selecting a region of interest, without selecting a tool for measuring a circumference or an area, the ultrasound apparatus 1000, may measure and provide the circumference or area of the region of interest. In addition, when a user input of selecting a coordinate is received, the ultrasound apparatus 1000 may provide a plurality of pieces of information of interest based on the selected coordinate.

FIG. 6 is a flowchart of a method of determining a measurement tool based on a coordinate selected by a user in the ultrasound apparatus 1000, according to an exemplary embodiment.

In operation S610, the ultrasound apparatus 1000 may display an ultrasound image on a screen. In operation S220, the ultrasound apparatus 1000 may receive a user input of selecting at least one coordinate on the ultrasound image.

In operation S630, the ultrasound apparatus 1000 may determine at least one measurement tool candidate based on a type and sequence of the received user input.

The ultrasound apparatus 1000 may compare the type and sequence of the received user input with preset input pattern information and determine at least one measurement tool.

The types of inputs and input sequences of pieces of input pattern information corresponding to a plurality of measurement tools may be identical to one another. Therefore, the ultrasound apparatus 1000 may determine the plurality of measurement tools based on a type and sequence of a user input received from a user.

In operation S640, the ultrasound apparatus 1000 may display a plurality of lines connecting the plurality of selected coordinates based on the type and sequence of the user input received.

In the ultrasound apparatus 1000, a method of generating a plurality of lines may be previously set corresponding to a type and sequence of a user input. For example, when user inputs of selecting four coordinates by clicking the four coordinates are received, a method of generating two line segments by connecting selected coordinates which is previously set and corresponds to the user inputs of selecting four coordinates may be implemented. When a user input of dragging across a plurality of consecutive coordinates is received, a method of generating an open curve by connecting the selected coordinates which is previously set and corresponds to the user input of dragging may be implemented.

The ultrasound apparatus 1000 may select a method of generating a plurality of lines which corresponds to the type and sequence of the received user input, from the memory. The ultrasound apparatus 1000 may generate and display a plurality of lines connecting the plurality of selected coordinates according to the selected method of generating a plurality of lines.

In operation S650, the ultrasound apparatus 1000 may determine one measurement tool from among at least one measurement tool candidate, based on information on intersection points between the plurality of displayed lines.

In the ultrasound apparatus 1000, a relationship between a plurality of lines may be previously set corresponding to a measurement tool. The relationship between a plurality of lines may include information on an intersection point. The information about an intersection point may include the number of intersection points, a position of an intersection point, and an intersection angle.

For example, the relationship of the plurality between lines which is set to correspond to a measurement tool for measuring an angle may be a relationship where one intersection point exists between two line segments, and an angle formed by the two line segments is equal to or smaller than a preset angle. For example, the relationship between the plurality of lines which is set to correspond to a measurement tool for measuring an oval may be a relationship where one intersection point exists between two line segments, and an angle formed by the two line segments is equal to or greater than a preset angle.

Therefore, the ultrasound apparatus 1000 may extract a relationship between a plurality of lines corresponding to the at least one measurement tool candidate determined in operation S630. The ultrasound apparatus 1000 may determine whether a relationship between the plurality of lines displayed in operation S630 is equal to the relationship between a plurality of lines which corresponds to the at least one measurement tool determined in operation S630.

The ultrasound apparatus 1000 may determine, from the at least one measurement tool candidate, one measurement tool which the relationship between the plurality of displayed lines corresponds to. For example, when the plurality of lines display are two line segments, the two line segments intersect each other, and an intersection angle between the two line segments is equal to or smaller than a present angle, the ultrasound apparatus 1000 may determine a measurement tool for measuring an angle as a measurement tool.

For example, when the plurality of lines displayed are two line segments and the two line segments do not intersect each other, the ultrasound apparatus 1000 may determine a measurement tool for measuring a ratio of lengths of a plurality of lines as a measurement tool. The ultrasound apparatus 1000 may provide a measurement tool for comparing stenosis diameters with one another.

In operation S660, the ultrasound apparatus 1000 may determine a region of interest based on the determined measurement tool and the at least one selected coordinate. In operation S670, the ultrasound apparatus 1000 may acquire information of interest from the determined region of interest according to the measurement tool.

For example, when a measurement tool for measuring an angle is determined, the ultrasound apparatus 1000 may determine a position at which an angle is to be measured. When a measurement tool for measuring an oval is determined, the ultrasound apparatus 1000 may determine a region of an oval to be measured. The ultrasound apparatus 1000 may measure information of interest corresponding to a measurement tool based on a preset measurement method.

Although a plurality of measurement tools may correspond to one type of a user input, the ultrasound apparatus 1000 may determine one measurement tool based on a coordinate selected by the user input.

FIGS. 7A to 7C and 8A to 8C are diagrams illustrating an example in which the ultrasound apparatus according to an exemplary embodiment determines a measurement tool based on a coordinate selected by a user.

The ultrasound apparatus 1000 may display a plurality of lines connecting a plurality of selected coordinates based on a type and sequence of a received user input. The ultrasound apparatus 1000 may determine at least one measurement tool based on the type and sequence of the received user input. In the ultrasound apparatus 1000, a relationship between the plurality of lines may be previously set corresponding to a measurement tool.

Therefore, the ultrasound apparatus 1000 may extract a relationship between a plurality of lines corresponding to the at least one determined measurement tool. The ultrasound apparatus 1000 may determine, from the at least one determined measurement tool, one measurement tool which the relationship between the plurality of displayed lines corresponds to.

Figure 7B:
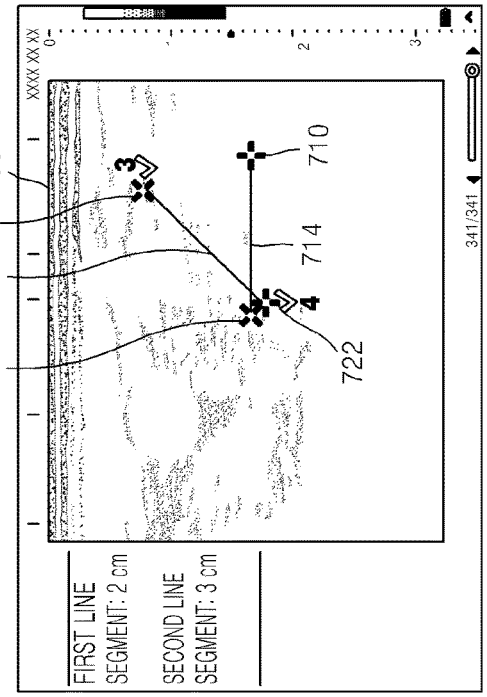
FIGS. 7A to 7C and 8A to 8C are diagrams illustrating an example in which an ultrasound apparatus according to an exemplary embodiment determines a measurement tool based on a coordinate selected by a user.
Figure 7A:
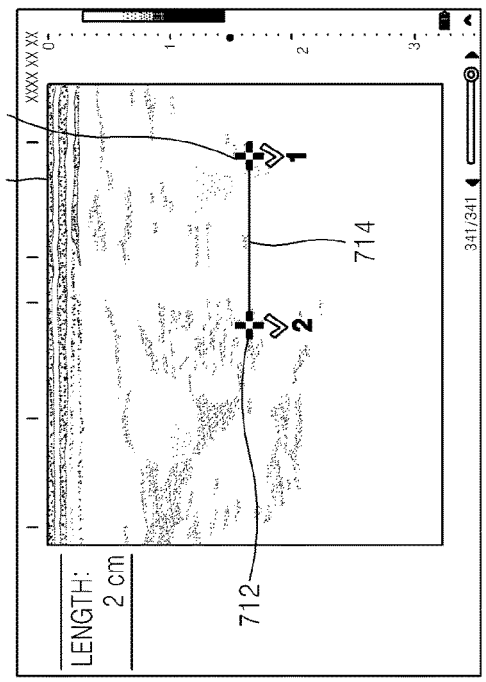
Figure 8B:
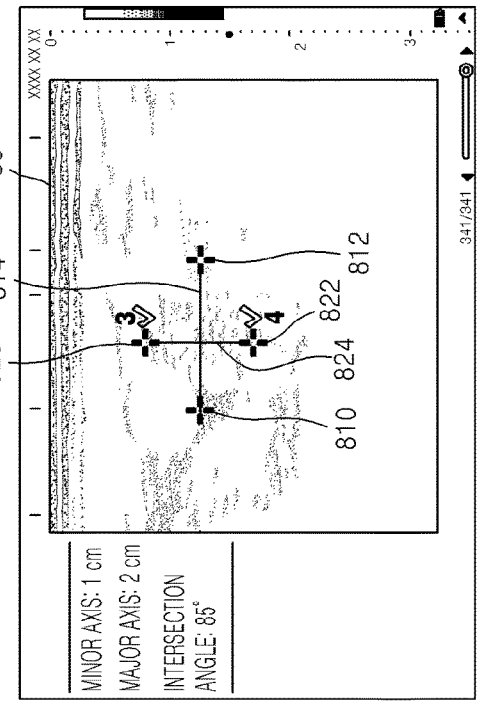
Figure 8A:
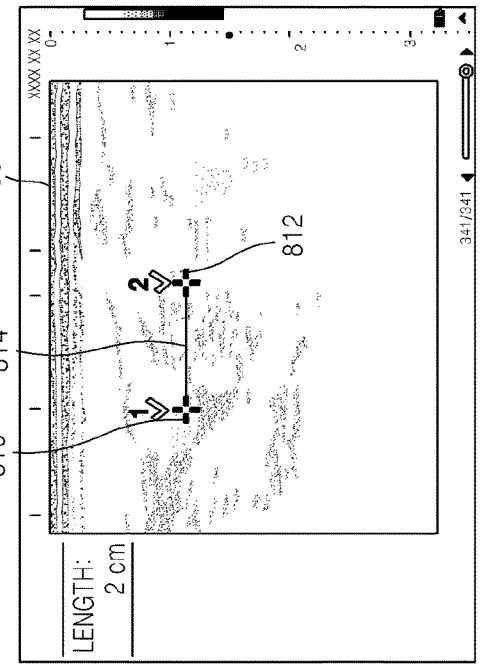

Referring to FIGS. 7A and 8A, the ultrasound apparatus 1000 may receive user inputs of clicking a first coordinate 710 or 810 and then clicking a second coordinate 712 or 812. In this case, the ultrasound apparatus 1000 may display a first line segment 714 or 814 connecting the first coordinate 710 or 810 and the second coordinate 712 or 812 corresponding to the first and second user inputs, the types of which are a click.

Referring to FIGS. 7B and 8B, in a state where a user selects the first coordinate 710 or 810 and the second coordinate 712 or 812, the ultrasound apparatus may receive user inputs of clicking a third coordinate 720 or 820 and continuously clicking a fourth coordinate 722 or 822. In this case, the ultrasound apparatus 1000 may display a second line segment 724 or 824 connecting the third coordinate 720 or 820 and the fourth coordinate 722 or 822.

On the other hand, a measurement tool for measuring an angle and a measurement tool for measuring an oval region may be previously set as measurement tools corresponding to an input pattern where the types of the first, second, third, and fourth user inputs are all clicks. Therefore, the ultrasound apparatus 1000 may compare the user inputs with a preset input pattern and determine the measurement tool for measuring an angle and the measurement tool for measuring an oval region as measurement tool candidates.

A relationship between the plurality of lines set corresponding to the measurement tool for measuring an angle may be a relationship where one intersection point exists between two line segments, and an angle formed by the two line segments is equal to or less than a preset angle. In addition, a relationship between the plurality of lines which is in advance set to correspond to the measurement tool for measuring an oval may be a relationship where one intersection point exists between two line segments, and an angle formed by the two line segments is equal to or greater than a preset angle.

Figure 7C:
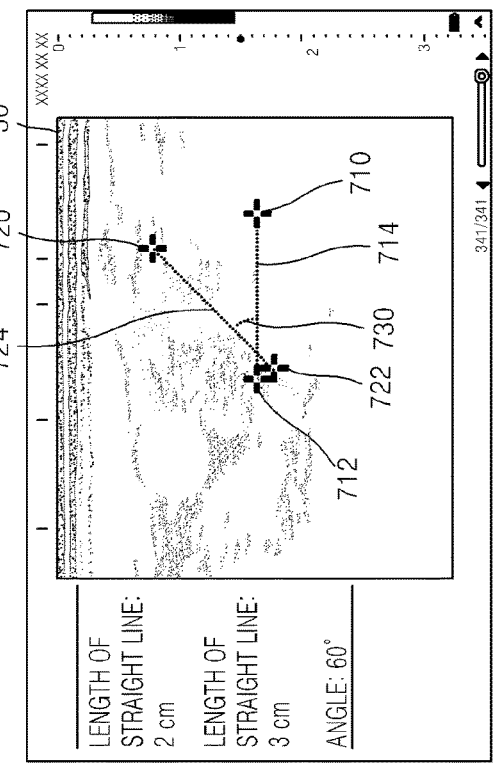

Referring to FIG. 7C, when an intersection angle between the first line segment 714 and the second line segment 724 is equal to or smaller than a preset angle (for example, 80°), the ultrasound apparatus 1000 may determine the measurement tool for measuring an angle as a measurement tool.

To this end, the ultrasound apparatus 1000 may determine the intersection point between the first line segment 714 and the second line segment 724 and measure the angle between the first line segment 714 and the second line segment 724 based on the calculated intersection point. The ultrasound apparatus 1000 may display the first line segment 714, the second line segment 724, and the measured intersection angle on a screen of the ultrasound apparatus 1000.

Figure 8C:
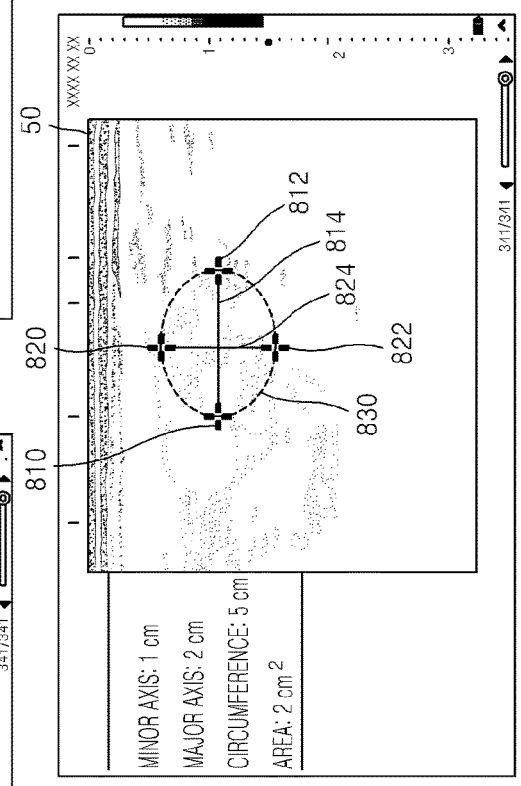

Referring to FIG. 8C, when an intersection angle between the first line segment 814 and the second line segment 824 is equal to or greater than a preset angle (for example, 80) and an intersection point between the first line segment 814 and the second line segment 824 is located within a predetermined distance from the center points of the first and second line segments, the ultrasound apparatus 1000 may determine the measurement tool for measuring an oval as a measurement tool.

In this case, the ultrasound apparatus 1000 may determine a region of an oval 830, of which the major axis is the longer of the first and second line segments and the minor axis is the shorter of the first and second line segments, as a region of interest. In addition, the ultrasound apparatus 1000 may measure a circumference and area of the determined oval 830. The ultrasound apparatus 1000 may display the first line segment 814, the second line segment 824, and the circumference and area of the oval 830 on a screen of the ultrasound apparatus 1000.

Figure 9B:
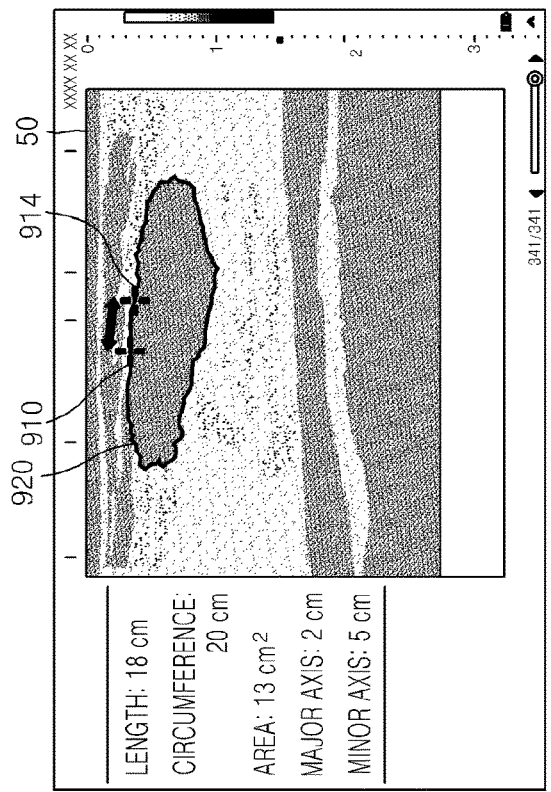
FIGS. 9A and 9B are diagrams illustrating an example in which an ultrasound apparatus according to an exemplary embodiment measures an area of a closed curve based on a user input.
Figure 9A:
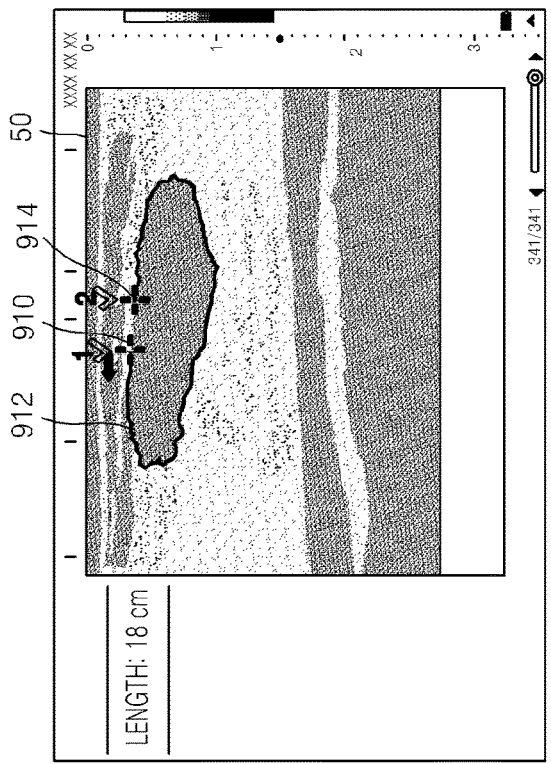

FIGS. 9A and 9B are diagrams illustrating an example in which the ultrasound apparatus 1000 according to an exemplary embodiment measures an area of a closed curve based on a user input.

Referring to FIG. 9A, the ultrasound apparatus may display a B mode ultrasound image showing a breast tumor.

The ultrasound apparatus 1000 may receive inputs of clicking a first coordinate 910, dragging from the first coordinate to a plurality of second coordinates along the boundaries of the tumor, and clicking a third coordinate 914 at a point at which dragging is terminated.

In correspondence to user inputs including a first input of which the type is a click, a second input of which the type is a drag input including a plurality of drags), and a third input of which the type is click, a method of displaying an open curve connecting the first input, the second input, and the third input which is previously set and corresponds to the first input, the second input, and the third input may be implemented. Therefore, the ultrasound apparatus 1000 may generate the open curve connecting the first, second and third inputs, and display the generated open curve on the screen of the ultrasound apparatus.

A measurement tool for measuring a characteristic of a closed curve may be previously set as a measurement tool corresponding to the input pattern including a first input of which the type is a click, a second input of which the type is a plurality of drags, and a third input, of which the type is click. The measurement tool for measuring the closed curve may further include a condition where a distance between both endpoints of the open curve is equal to or smaller than a predetermined distance, in addition to the preset input pattern.

Referring to FIG. 9A, when the distance between a first coordinate 910 and a second coordinate 914 is equal to or smaller than the predetermined distance, the ultrasound apparatus 1000 may select, as a measurement tool, a measurement tool for measuring a circumference or area of a closed curve generated by connecting the first coordinate and the third coordinate.

The ultrasound apparatus 1000 may generate a closed curve by connecting the first coordinate 910 and the third coordinate 914 based on the generated open curve. In addition, the ultrasound apparatus 1000 may measure a circumference and area of the closed curve 920.

The ultrasound apparatus 1000 may display the shape, circumference, and area of the closed curve 920 on the screen of the ultrasound apparatus 1000.

Although not illustrated, the ultrasound apparatus 1000 may generate a plurality of closed curves according to a user input. When a first closed curve includes a second closed curve, the ultrasound apparatus may select a tool for measuring a ratio of areas of the first closed curve and the second closed curve. The ultrasound apparatus 1000 may provide a measurement tool for comparing stenosis areas with one another.

Although the shape of the object is not uniform, for example, as in breast tumor, the user may measure information of interest by merely selecting a region of interest without selecting a separate measurement tool.

FIGS. 10A to 10D are diagrams illustrating an example in which the ultrasound apparatus 1000 according to an exemplary embodiment measures a volume based on a user input.

Figure 10B:
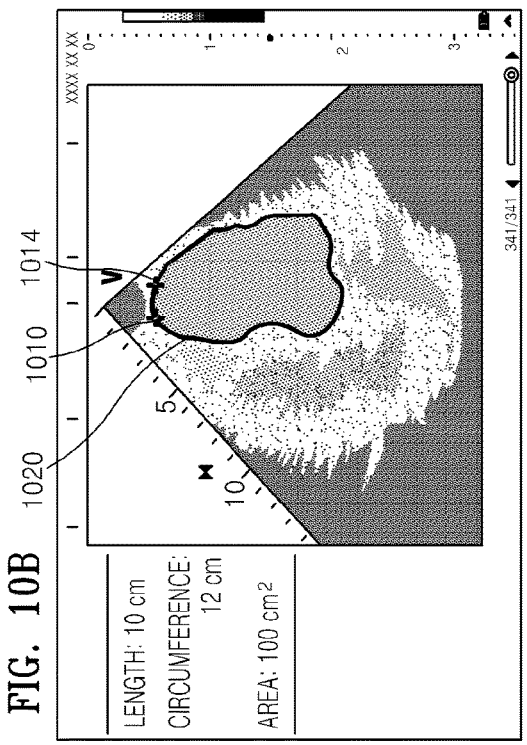
FIGS. 10A to 10D are diagrams illustrating an example in which an ultrasound apparatus according to an exemplary embodiment measures a volume based on a user input.
Figure 10D:
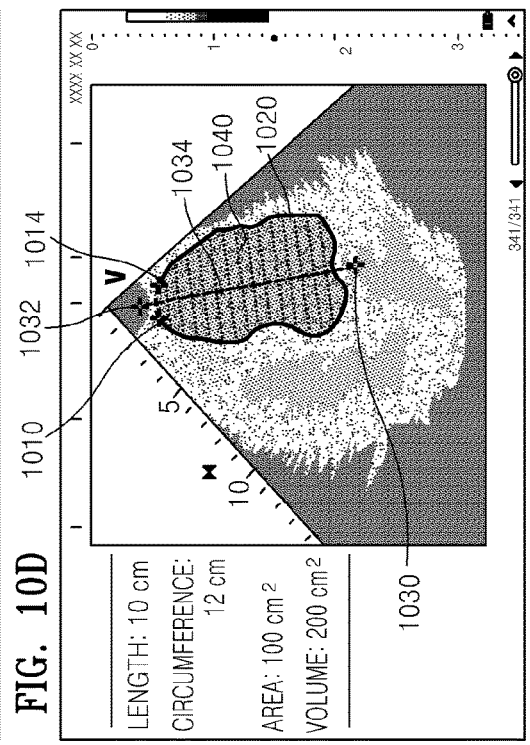
Figure 10A:
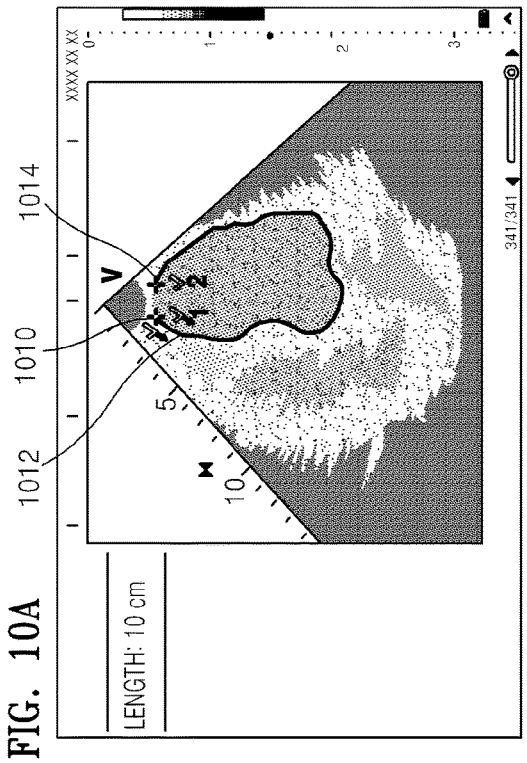

Referring to FIG. 10A, the ultrasound apparatus 1000 may display a B mode ultrasound image showing a heart.

When a user click a first coordinate 1010, drags from the first coordinate to a plurality of second coordinates along the boundaries of the heart's atrium, and clicks a third coordinate 1014 at a point at which the drag is terminated, the ultrasound apparatus 1000 may determine whether a distance from the first coordinate 1010 to the third coordinate 1014 is equal to or smaller than a predetermined distance.

Referring to FIG. 10B, when the distance from the first coordinate to the third coordinate 1014 is equal to or smaller than the predetermined distance, the ultrasound apparatus may select a measurement tool for measuring a circumference or area of a closed curve 1020 which may be generated according to the first coordinate 1010 to the third coordinate 1014 as a measurement tool corresponding to the input pattern.

Figure 10C:
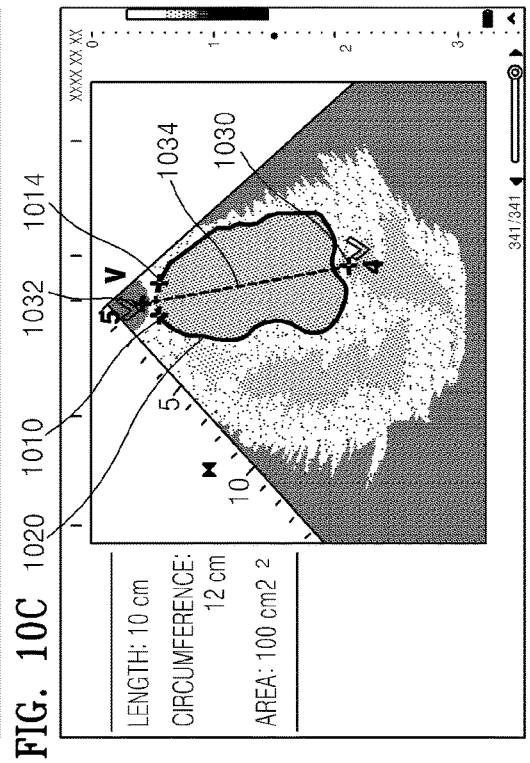

Referring to FIG. 10C, in a state in which the closed curve is generated, the ultrasound apparatus 1000 may receive user inputs of clicking a fourth coordinate 1030 and then clicking a fifth coordinate 1032. According to a preset method of displaying a line segment, the ultrasound apparatus 1000 may generate a line segment 1034 connecting the fourth coordinate 1030 and the fifth coordinate 1032, and display the line segment 1034.

In the state in which the closed curve is generated, two consecutive click inputs may be a preset input pattern corresponding to the measurement tool for measuring a volume. A condition that there are two intersection points between the closed curve and the line segment generated by the two click inputs may be previously set corresponding to the measurement tool for measuring a volume.

When the inputs of selecting the fourth coordinate 1030 and the fifth coordinate 1032 are received, the ultrasound apparatus 1000 may determine the measurement tool for measuring a volume as a measurement tool candidate. The ultrasound apparatus 1000 may determine whether there are two intersection points between the closed curve 1020 and the line segment. When there are two intersection points between the closed curve 1020 and the line segment 1034, the ultrasound apparatus 1000 may determine the measurement tool for measuring volume as a measurement tool.

The ultrasound apparatus 1000 may generate a predetermined number of straight lines 1040 perpendicular to the line segment 1034 within the closed curve at uniform intervals based on a preset method (for example, The Rule of Disks or Simpson's Rule) of measuring a volume. The ultrasound apparatus 1000 may generate cylinders each having a diameter defined by the length of each of the straight lines 1040 and a height defined by a distance between the straight lines 1040. The ultrasound apparatus 1000 may measure volumes of the generated cylinders and measure a volume of an area of the closed curve 1020 in addition to the measured volumes.

The ultrasound apparatus 1000 may display the shape and volume of the closed curve 1020 on a screen of the ultrasound apparatus 1000.

Figure 11:
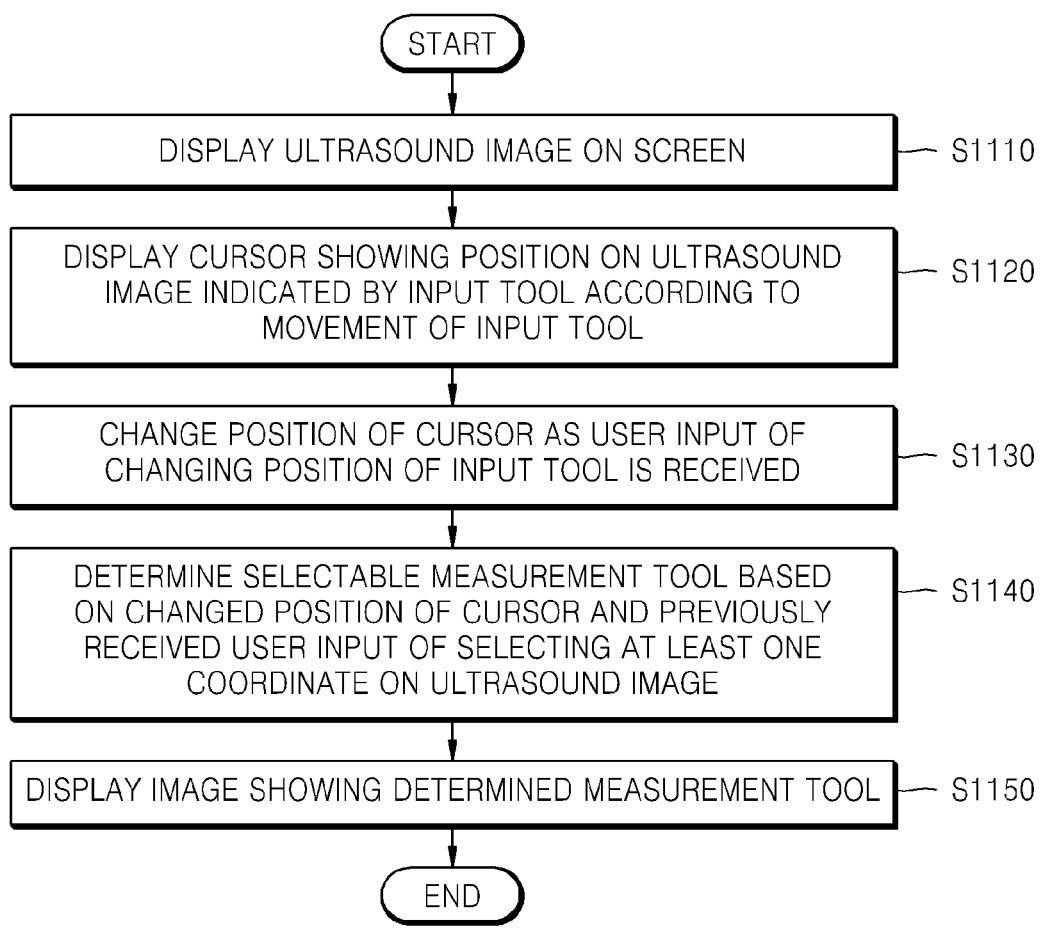
FIG. 11 is a flowchart of a method of displaying selectable measurement tools in an ultrasound apparatus as an input tool is moved, according to an exemplary embodiment.

FIG. 11 is a flowchart of a method of displaying selectable measurement tools in the ultrasound apparatus 1000 as an input tool is moved, according to an exemplary embodiment.

In operation S1110, the ultrasound apparatus 1000 may display an ultrasound image on a screen.

In operation S1120, the ultrasound apparatus 1000 may display a cursor on the ultrasound image that indicates a position of the input tool. For example, the ultrasound apparatus 1000 may display a cursor showing movement of the input tool on the screen of the ultrasound apparatus 1000. The cursor may show the position of the input tool with respect to the ultrasound image. The input tool may include a trackball, a mouse, a finger or the like, but is not limited thereto.

In operation S1130, the ultrasound apparatus 1000 may change a position of the cursor when a user input of changing a position of the input tool is received.

For example, when the user moves a trackball provided with a control panel, the position of the cursor displayed on the ultrasound image may be changed.

In operation S1140, the ultrasound apparatus 1000 may determine a selectable measurement tool based on the changed position of the cursor and a received user input of selecting at least one coordinate on the ultrasound image.

In the state where at least one coordinate is selected, when the user moves the cursor by using the input tool, without selecting a specific coordinate, the ultrasound apparatus 1000 may determine a selectable measurement tool based on a changed coordinate of the cursor and at least one selected coordinate.

When the user selects a coordinate at which the cursor is located, the ultrasound apparatus 1000 may identify the selectable measurement tool based on the coordinate of the cursor, and at least one other coordinate which is already selected.

The ultrasound apparatus 1000 may not determine a measurement tool when a received input is insufficient to determine a measurement tool.

In operation S1150, the ultrasound apparatus may display an image showing the determined measurement tool on the screen of the ultrasound apparatus 1000.

For example, the ultrasound apparatus 1000 may determine a region of interest corresponding to the determined measurement tool based on the coordinate of the cursor and the at least one coordinate which is preselected. The ultrasound apparatus 1000 may display the determined region of interest on the screen of the ultrasound apparatus 1000.

The display may inform the user of a selectable measurement tool and a selectable region of interest as the cursor is moved, allowing the user to conveniently analyze the ultrasound image.

Figure 12A:
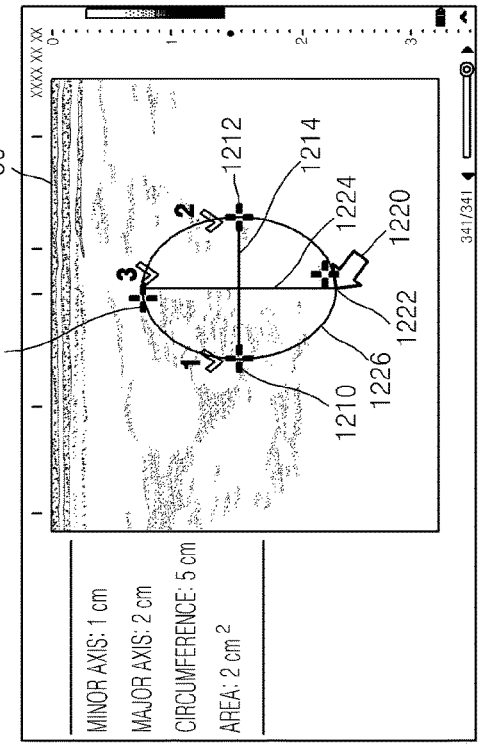
FIGS. 12A to 12C are diagrams illustrating an example in which an ultrasound apparatus displays selectable measurement tools based on a coordinate of a cursor, according to an exemplary embodiment.
Figure 12B:
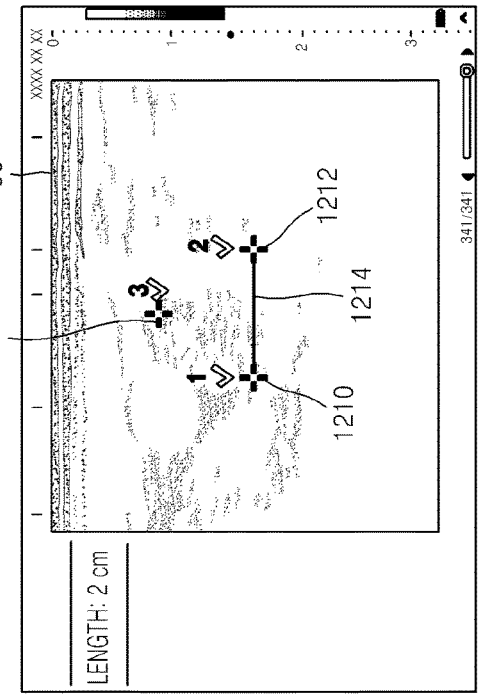
Figure 12C:
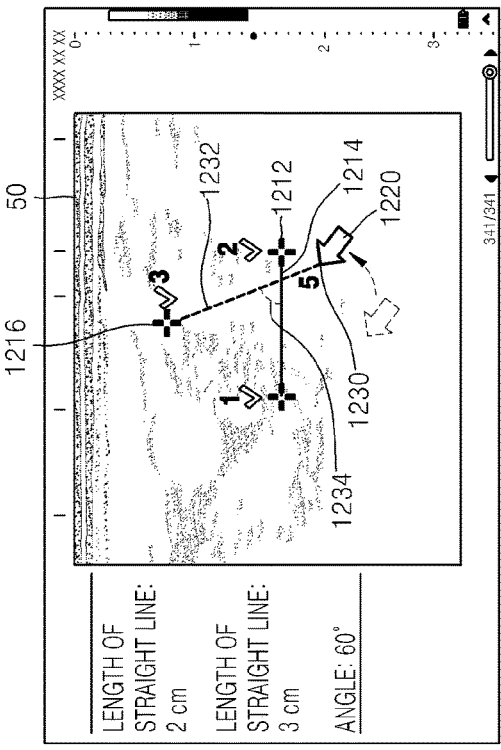

FIGS. 12A to 12C are diagrams illustrating an example in which the ultrasound apparatus 1000 displays selectable measurement tools based on a coordinate of a cursor, according to an exemplary embodiment.

When a user clicks a first coordinate 1210, clicks a second coordinate 1212, and clicks a third coordinate 1216, the ultrasound apparatus 1000 may determine whether there is a measurement tool corresponding to an input pattern where the types of the first to third user inputs are all a click. When no measurement tool corresponds to the received input pattern, the ultrasound apparatus 1000 may not determine a measurement tool.

Referring to FIG. 12B, the ultrasound apparatus 1000 may display a cursor 1220 on a screen of the ultrasound apparatus 1000.

The ultrasound apparatus 1000 may display the cursor at a fourth coordinate 1222 as an input tool is moved by a user. The ultrasound apparatus 1000 may determine selectable measurement tools based on the first coordinate 1210 to the fourth coordinate 1222 as the cursor 1220 is moved to the fourth coordinate 1222.

When the fourth coordinate 1222 is selected, the ultrasound apparatus 1000 may determine that a measurement tool for measuring information on an oval, of which the minor axis is a line segment 1214 connecting the first coordinate 1210 and the second coordinate 1212 and the major axis is a line segment 1214 connecting the third coordinate 1216 and the fourth coordinate 1222, as a measurement tool.

The ultrasound apparatus 1000 may display information indicating that a measurement tool for measuring an oval may be selectable based on the current position of the cursor on the screen of the ultrasound apparatus 1000.

For example, the ultrasound apparatus 1000 may display the determined oval 1226 based on the position of the cursor and the at least one coordinate which is preselected. In this case, the ultrasound apparatus 1000 may use a different type of line to display the oval 1226 such that the oval 1226 displayed before the fourth coordinate 1222 is selected may be distinguished from an oval displayed when the fourth coordinate 1222 is selected.

Even when the coordinate at which the cursor is located is not selected, the ultrasound apparatus 1000 may measure information of interest which may be measured upon selection of the coordinate and display the information. The ultrasound apparatus 1000 may measure a length of the major axis or minor axis of the determined oval 1226, a circumference of the oval 1226, and an area of the oval 1226. The ultrasound apparatus 1000 may display the measured information on the screen of the ultrasound apparatus 1000.

Referring to FIG. 12C, as the input tool is continuously moved by the user, the ultrasound apparatus 1000 may display the cursor at a fifth coordinate 1230. The ultrasound apparatus 1000 may determine a selectable measurement tool based on the first coordinate 1210 to the third coordinate 1216 and the fifth coordinate 1230 as the cursor 1220 is moved to the fifth coordinate 1230.

When the fifth coordinate 1230 is selected, the ultrasound apparatus 1000 may determine a measurement tool for measuring an intersection angle between a line segment 1214 connecting the first coordinate 1210 and the second coordinate 1212 and a line segment 1232 connecting the third coordinate 1216 and the fifth coordinate 1230 as a measurement tool.

The ultrasound apparatus 1000 may display information indicating that a measurement tool for measuring an angle is selectable based on the current position of the cursor on the screen of the ultrasound apparatus 1000. For example, the ultrasound apparatus 1000 may display an angle indicator 1234 representing an intersection point of interest based on the position of the cursor and the at least one coordinate which is already selected.

Even when the user does not select the fifth coordinate 1230, the ultrasound apparatus 1000 may measure an angle at the intersection point. The ultrasound apparatus 1000 may display information on the measured angle on the screen of the ultrasound apparatus 1000.

The user may identify a selectable measurement tool as the cursor is moved, allowing the user to conveniently measure the ultrasound image. The user may check measured information of interest as the cursor is moved, allowing the user to rapidly check information of interest without repeatedly selecting coordinates.

Figure 13:
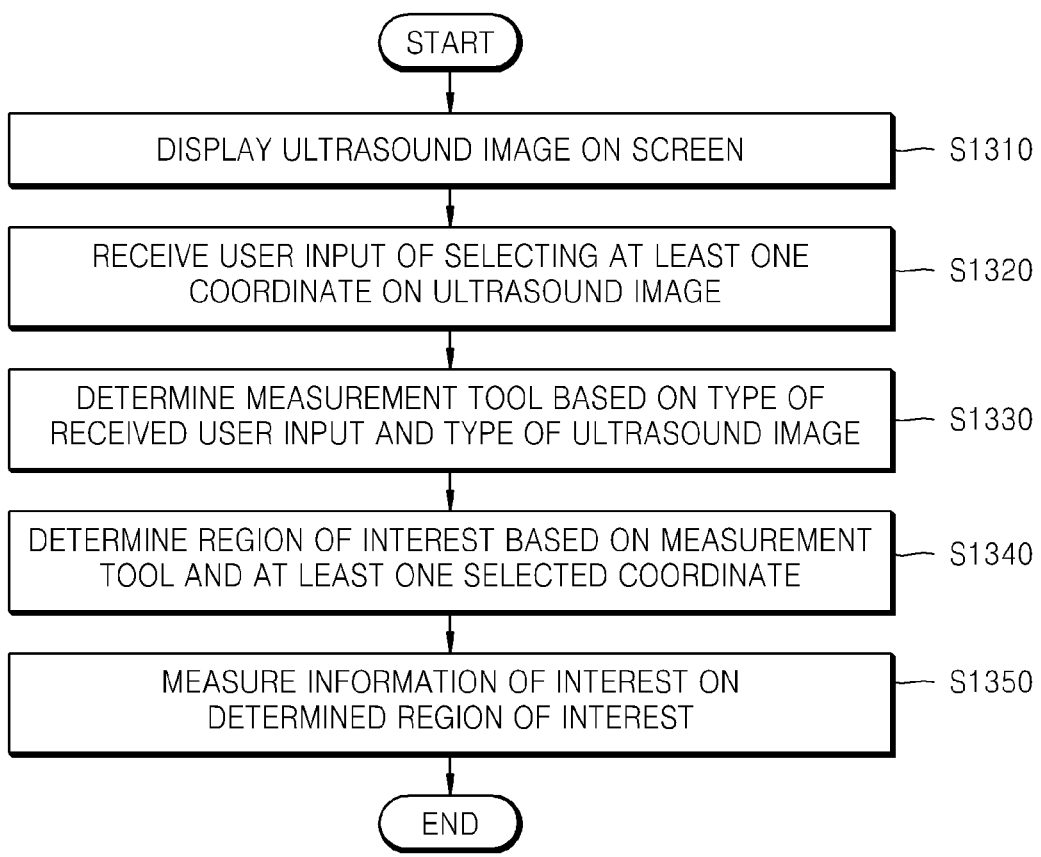
FIG. 13 is a flowchart of a method of determining a measurement tool based on a received user input and a type of an ultrasound image in an ultrasound apparatus, according to an exemplary embodiment.

FIG. 13 is a flowchart of a method of determining a measurement tool based on a received user input and a type of an ultrasound image in the ultrasound apparatus 1000, according to an exemplary embodiment.

In operation S1310, the ultrasound apparatus 1000 may display an ultrasound image on a screen. The ultrasound image may include at least one of a B mode image, a C mode image, and a Doppler mode image, but is not limited thereto.

In operation S1320, the ultrasound apparatus 1000 may receive a user input of selecting at least one coordinate on the ultrasound image.

In operation S1330, the ultrasound apparatus 1000 may determine a measurement tool based on the received user input and a type of the ultrasound image.

Generally, the B mode image uses brightness to represent a magnitude of an echo signal reflected from an object. That is, the B mode image is an image representing a shape or movement of the object. When the B mode image is displayed, the ultrasound apparatus 1000 may be set to select a measurement tool associated with the shape of the object.

In addition, a color mode image uses colors to represent a velocity of a moving object by using the Doppler effect. That is, the color mode image uses colors to represent a movement velocity and direction of the object. Generally, the movement velocity and direction of the object of the color mode image are displayed by colors directly in a region of the B mode image in which the object is displayed. Therefore, when the cooler mode image is displayed, the ultrasound apparatus 1000 may be set to select a measurement tool for providing a movement velocity and direction of an object, based on a user input of selecting a B mode image region.

The Doppler mode image represents an image of a moving object in a spectrum form by using a Doppler effect. That is, the Doppler mode image is an image showing a graph of velocity versus time indicating a change in velocity of an object with respect to a specific point of the object. When the Doppler mode image is displayed, the ultrasound apparatus 1000 may be set to select a measurement tool for measuring a velocity at a selected time point, a movement distance over a selected time interval, and waveform analysis of the graph.

In addition, the M mode image shows movement of an object with time with respect to a specific position of the object. That is, the M mode image is an image showing a change in movement of the object with time with respect to a specific cross-section of the object. Therefore, when the M mode image is displayed, the ultrasound apparatus 1000 may be set to select a measurement tool for measuring a length of a cross-section measured at a selected time or a ratio of lengths of the cross-section.

Although the ultrasound apparatus 1000 receives user inputs which are the same as each other, the ultrasound apparatus may select different measurement tools depending on a type of an ultrasound image displayed on the screen.

When a user input of selecting two coordinates on a B mode image is received, the ultrasound apparatus 1000 may determine the measurement tool for measuring a length of a straight line. When a user input of selecting two coordinates on a Doppler image is received, the ultrasound apparatus 1000 may determine a measurement tool for measuring a ratio of velocities corresponding to the selected coordinates.

In operation S134, the ultrasound apparatus 1000 may determine a region of interest based on the determined measurement tool and the at least one selected coordinate. In operation S1350, the ultrasound apparatus 1000 may measure information of interest on the region of interest.

FIG. 14 is a diagram illustrating an example in which the ultrasound apparatus 1000 according to an exemplary embodiment measures velocity information on the Doppler image based on a user input.

Figure 14A:
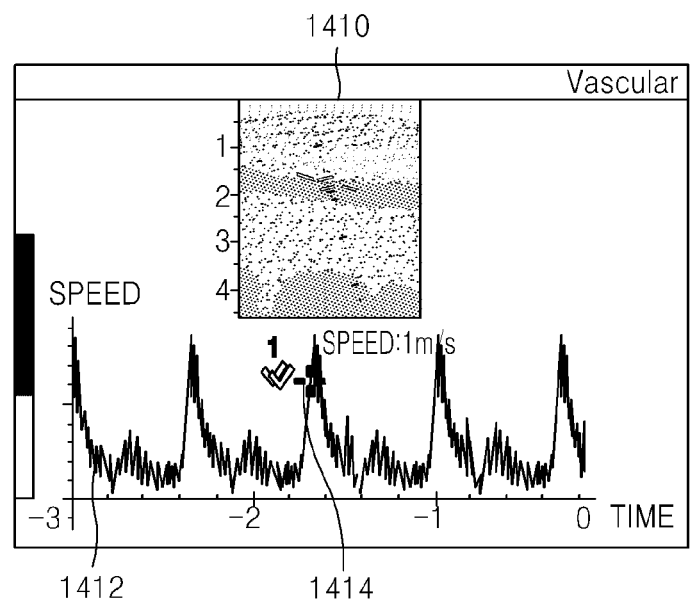
FIGS. 14A and 14B are diagrams illustrating an example in which an ultrasound apparatus according to an exemplary embodiment measures velocity information from the Doppler image based on a user input.
Figure 14B:
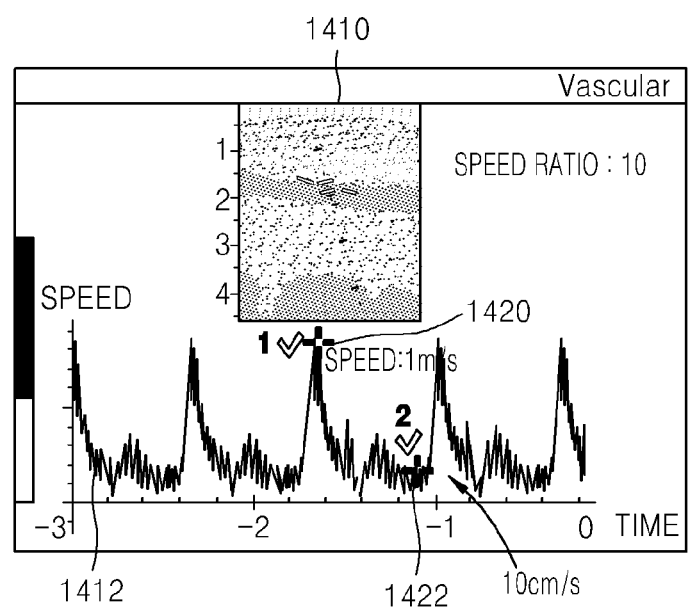

Referring to FIGS. 14A and 14B, the ultrasound apparatus 1000 may display a B mode image 1410 of a blood vessel on a screen of the ultrasound apparatus 1000. The ultrasound apparatus 1000 may display a Doppler spectrum graph 1412 showing a blood flow through the blood vessel, which is displayed on the B mode image 1410, on the screen.

Referring to FIG. 14A, the ultrasound apparatus 1000 may receive a user input of double clicking a first coordinate 1414. When the ultrasound image displayed on the screen includes a Doppler spectrum graph 1412, the ultrasound apparatus 1000 may determine whether the first coordinate 1414 is located on the Doppler spectrum graph 1412. When the first coordinate 1414 is located on the Doppler spectrum graph 1412, the ultrasound apparatus 1000 may display a blood flow velocity corresponding to the first coordinate 1414 at a time point on the Doppler spectrum graph 1412 on the screen.

Referring to FIG. 14B, the ultrasound apparatus 1000 may receive user inputs of clicking a first coordinate 1420 and then clicking a second coordinate 1422. When the ultrasound image displayed on the screen includes a Doppler spectrum graph 1412, the ultrasound apparatus 1000 may determine whether the first coordinate 1420 and the second coordinate 1422 are located on the Doppler spectrum graph 1412. When the first coordinate 1420 and the second coordinate 1422 are located on the Doppler spectrum graph 1412, the ultrasound apparatus 1000 may measure a velocity ratio of a blood flow velocity corresponding to the first coordinate 1420 to a blood flow velocity corresponding to the second coordinate 1422 on the Doppler spectrum graph 1412. In addition, the ultrasound apparatus 1000 may display the measured velocity ratio on the screen.

FIG. 15 is a diagram illustrating an example in which the ultrasound apparatus 1000 according to an exemplary embodiment measures a movement distance of an object and an envelope of a waveform on a Doppler image based on a user input.

Figure 15A:
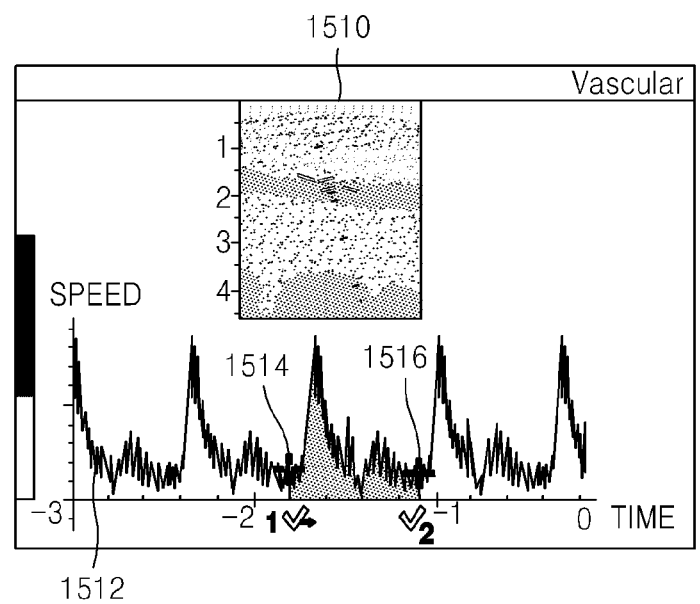
FIGS. 15A and 15B are diagrams illustrating an example in which an ultrasound apparatus according to an exemplary embodiment measures a movement distance of an object and an envelope of waveform from a Doppler image based on a user input.
Figure 15B:
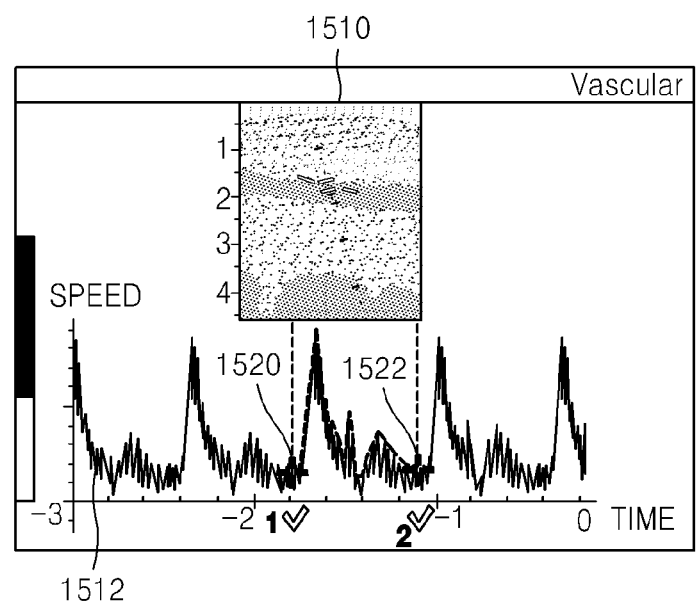

Referring to FIGS. 15A and 15B, the ultrasound apparatus 1000 may display a B mode image 1510 of a blood vessel on a screen of the ultrasound apparatus 1000. The ultrasound apparatus 1000 may display a Doppler spectrum graph 1512 showing a blood flow through the blood vessel, which is displayed on the B mode image 1510, on the screen.

Referring to FIG. 15A, the ultrasound apparatus 1000 may receive a user input of clicking a first coordinate 1514, drag into a second coordinate 1516. When the displayed ultrasound image includes a Doppler spectrum graph 1512, the ultrasound apparatus 1000 may determine the first coordinate 1514 and the second coordinate 1516 and may select a measurement tool for measuring a distance which blood moves over a time interval of the Doppler spectrum graph 1512 corresponding to the first coordinate 1514 and the second coordinate 1516 as a measurement tool.

Therefore, the ultrasound apparatus 1000 may determine the time interval corresponding to the first coordinate 1514 and the second coordinate 1516 on the Doppler spectrum graph 1512 as a time interval as interest. In addition, the ultrasound apparatus 1000 may measure the movement distance by integrating the blood flow velocity with the time interval of interest. In addition, the ultrasound apparatus 1000 may display the time interval of interest and the measured movement distance on the screen of the ultrasound apparatus 1000.

Referring to FIG. 15B, the ultrasound apparatus 1000 may receive user inputs of double clicking a first coordinate 1520 and then clicking a second coordinate 1522. When the displayed ultrasound image includes a Doppler spectrum graph 1512, the ultrasound apparatus 1000 may determine whether the first coordinate 1520 and the second coordinate 1522 are located on Doppler spectrum graph 1512 and may determine a measurement tool for measuring an envelope of the Doppler spectrum graph 1512 over a time interval corresponding to the first coordinate 1520 and the second coordinate 1522 on the Doppler spectrum graph 1512 and displaying the envelope on a screen thereof as a measurement tool.

Therefore, the ultrasound apparatus 1000 may determine the time interval corresponding to the first coordinate 1520 and the second coordinate 1522 on the Doppler spectrum graph 1512 as a time interval as interest. In addition, the ultrasound apparatus 1000 may measure the envelope by connecting peaks of the Doppler spectrum graph 1512 included in the time interval of interest to one another. In addition, the ultrasound apparatus 1000 may display the time interval of interest and the measured envelope of the waveform on the screen of the ultrasound apparatus 1000.

Figure 16A:
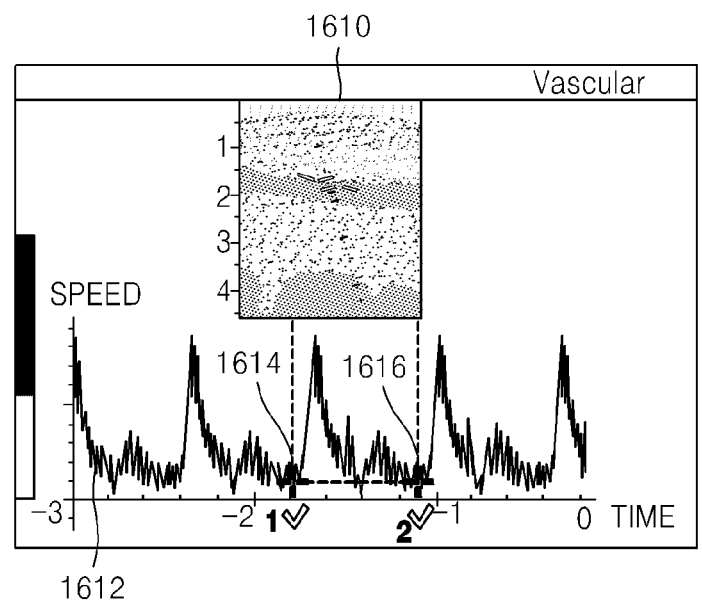
FIGS. 16A and 16B are diagrams illustrating an example in which an ultrasound apparatus according to an exemplary embodiment measures a time based on a user input.
Figure 16B:
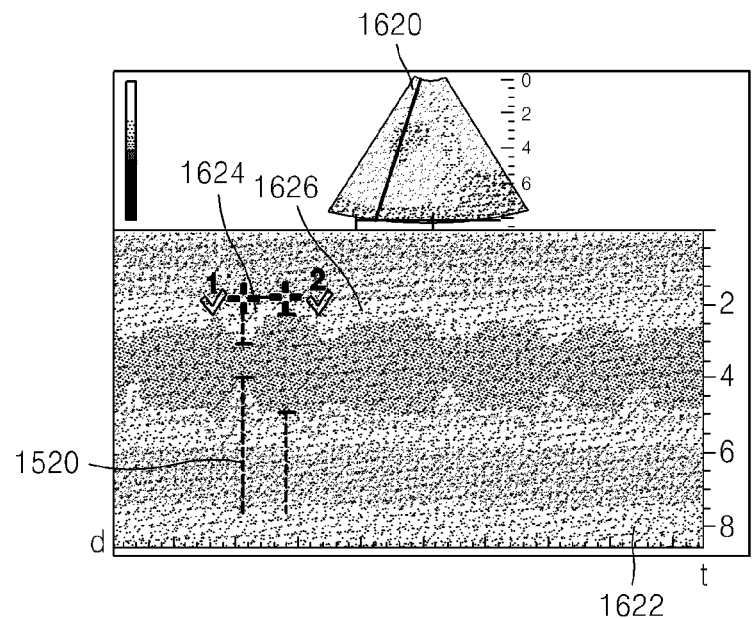

FIGS. 16A and 16B are diagrams illustrating an example in which the ultrasound apparatus 1000 according to an exemplary embodiment measures time based on a user input.

Referring to FIG. 16A, the ultrasound apparatus 1000 may display a B mode image 1610 of a blood vessel on a screen of the ultrasound apparatus 1000. The ultrasound apparatus 1000 may display a Doppler spectrum graph 1612 showing a blood flow through the blood vessel, which is displayed on the B mode image 1610.

The ultrasound apparatus 1000 may receive user inputs of clicking a first coordinate 1614 and clicking a second coordinate 1616. When the displayed ultrasound image includes a Doppler spectrum graph 1612, the ultrasound apparatus 1000 may determine a measurement tool for measuring a time interval corresponding to the first coordinate 1614 and the second coordinate 1616 on the Doppler spectrum graph 1612 as a measurement tool.

Therefore, the ultrasound apparatus 1000 may measure time information on the time interval corresponding to the first coordinate 1614 and the second coordinate 1616 on the Doppler spectrum graph 1612.

Referring to FIG. 16B, the ultrasound apparatus 1000 may display a B mode image 1620 of a heart on the screen of the ultrasound apparatus 1000. The ultrasound apparatus 1000 may display an M mode image 1622 showing a specific cross-section of the heart displayed on the B mode image 1620, together with the B mode image.

The ultrasound apparatus 1000 may receive a user input of selecting a first coordinate 1624 and a second coordinate 1626. When the displayed ultrasound image includes the M mode image 1622, the ultrasound apparatus 1000 may determine a measurement tool for measuring a time interval corresponding to the first coordinate 1624 and the second coordinate 1626 on the M mode image 1622 as a measurement tool. The ultrasound apparatus 1000 may determine a measurement tool for measuring how long an object extend (for example, a diastolic volume of a heart) at the time points corresponding to the first coordinate 1624 and the second coordinate 1626 on the M mode image 1622 as a measurement tool.

Therefore, the ultrasound apparatus 1000 may measure time information on the time interval corresponding to the first coordinate 1624 and the second coordinate 1626 on the M mode image 1622. In addition, the ultrasound apparatus 1000 may measure the extension degree of an object at the time points corresponding to the first coordinate 1624 and the second coordinate 1626 on the M mode image 1622.

Figure 17:
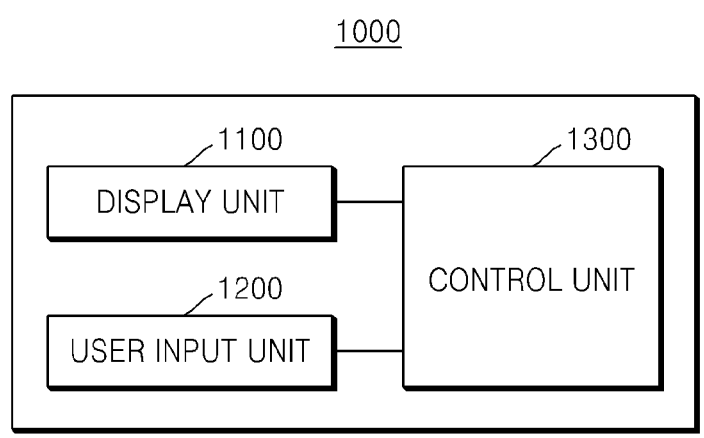
FIG. 17 is a block diagram illustrating a configuration of an ultrasound apparatus according to an exemplary embodiment.

FIG. 17 is a block diagram illustrating a configuration of the ultrasound apparatus 1000 according to an exemplary embodiment.

The ultrasound apparatus 1000 according to the exemplary embodiment may include a display unit 1110, a user input unit 1200, and a control unit 1300. However, not all of the illustrated components are necessary. The ultrasound apparatus 1000 may include more components than the illustrated components, and may include less components than the illustrated components.

The above components will be described below.

The display unit 1100 and a touchpad may be configured in a layered structure to constitute a touchscreen. That is, the display unit 1100 according to the exemplary embodiment may be used as not only an output device but also an input device.

The display unit 1100 may display an ultrasound image on a screen of the ultrasound apparatus 1000. The display unit 1100 may display a user interface for measuring the ultrasound image on the screen of the ultrasound apparatus 1000.

The display unit 1100 may display a user input of selecting at least one coordinate on the ultrasound image.

The user input unit 1200 may include a unit that allows the user to input data for controlling the ultrasound apparatus 1000. For example, the user input unit 1200 may include a control panel, a key pad, a dome switch, a touchpad (a contact capacitive method, a pressure resistive method, an infrared detection method, a surface acoustic wave method, an integral strain gauge method, a piezoelectric method, etc.), a touchscreen, a jog wheel, and a jog switch, but is not limited thereto. When the touch pad and the display panel are configured in a layered structure as described above, it may be referred to as a touchscreen. The user input unit 1200 according to an exemplary embodiment may detect a real-touch and a proximity touch.

The user input unit 1200 may receive a user input of selecting at least one coordinate on the ultrasound image. The user input unit 1200 may detect a touch input on the ultrasound image. The user input unit 1200 may detect a multi-touch input (for example, a pinch) on at least two points included in the ultrasound image.

The control unit 1300 may generally control overall operation of the ultrasound apparatus 1000. That is, the control unit 1300 may generally control the display unit 1100 and the user input unit 1200.

The control unit 1300 may determine a measurement tool corresponding to a user input based on a type of the user input.

For example, the control unit 1300 may compare the type of the user input with preset input pattern information. The control unit 1300 may determine the measurement tool corresponding to the user input based on a result of comparison of the type of the user input with the preset input pattern information.

The control unit 1300 may determine a measurement tool in consideration of a type of the ultrasound image.

The control unit 1300 may compare the type of the user input with the preset input pattern information and determine the measurement tool corresponding to the user input based on a result of the comparison.

The control unit 1300 may display a plurality of lines by using at least one coordinate as a reference according to a user input, and determine the measurement tool based on at least one of the number of intersection points between the plurality of displayed lines, a position of an intersection point, and an intersection angle. The control unit 1300 may measure at least one of a length and slope of each of the plurality of displayed lines. The control unit 1300 may measure an intersection angle between a plurality of straight lines.

The control unit 1300 may determine a region of interest based on at least one coordinate and measure at least one of an area and circumference of the determined region of interest.

When the ultrasound image is a spectral Doppler image, the control unit 1300 may acquire velocity information on the spectral Doppler image by using the determined measurement tool.

When the ultrasound image is a spectral Doppler image, the control unit 1300 may select a partial time interval on the spectral Doppler image based on the at least one coordinate, and measure at least one of a distance which blood moves or a distance which tissue moves over the time interval and an envelope of spectral waveform on the spectral Doppler image.

Figure 18:
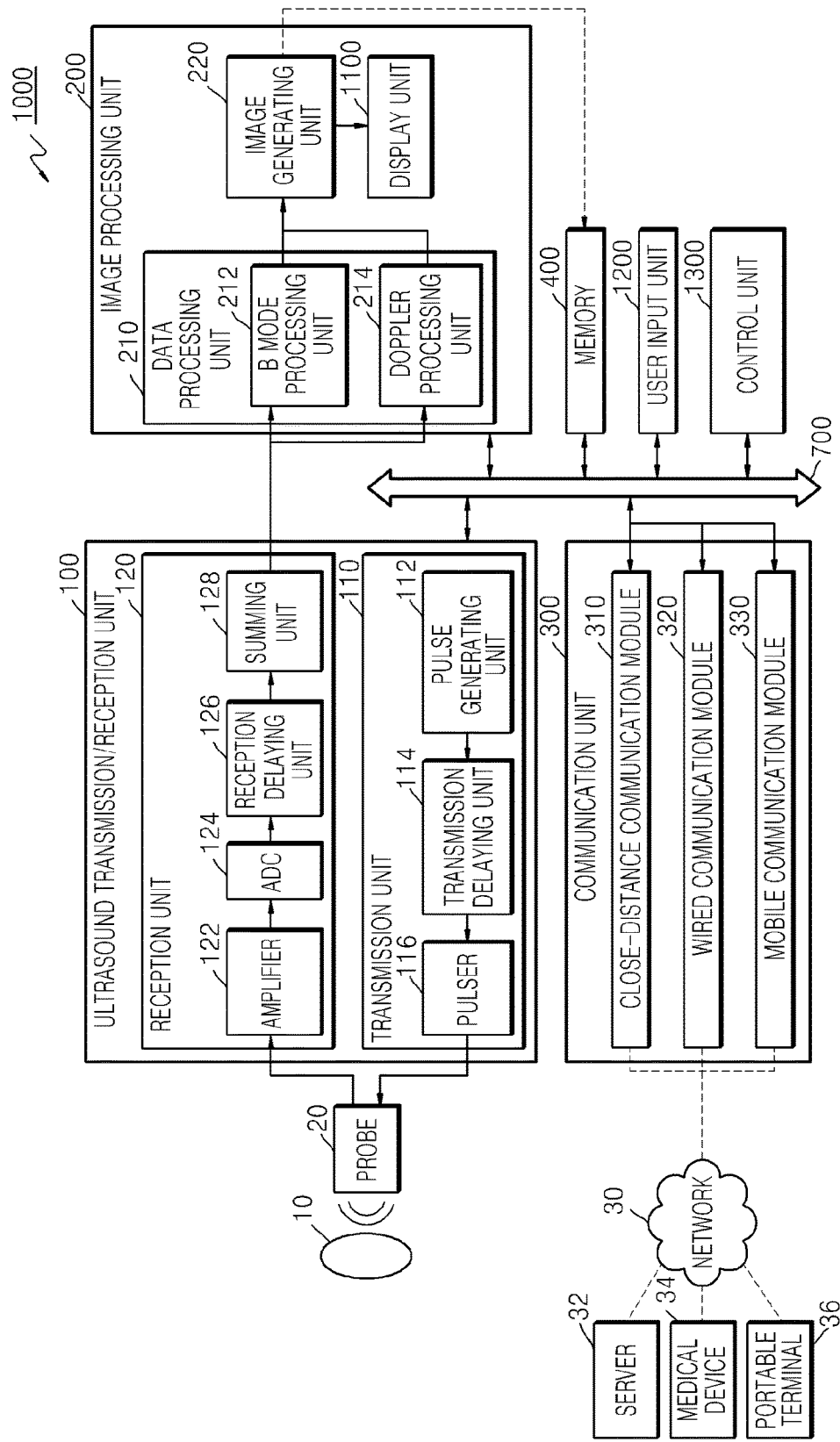
FIG. 18 is a block diagram illustrating a configuration of an ultrasound apparatus according to another exemplary embodiment.

FIG. 18 is a block diagram illustrating a configuration of an ultrasound apparatus according to another exemplary embodiment.

The ultrasound apparatus 1000 according to the exemplary embodiment may further include a probe 20, an ultrasound transmission and reception unit 100, an image processing unit 200, a communication unit 300, and a memory 400 in addition to the display unit 1110, the user input unit 1200, and the control unit 1300. The above components may be connected to one another via a bus 700.

The ultrasound apparatus 1000 may be implemented in a cart form or in a portable form. Examples of a portable ultrasound apparatus may include a picture archiving and communication system (PACS) viewer, a smart phone, a laptop computer, a personal digital assistant (PDA), a tablet personal computer (PC), but is not limited thereto.

The probe 20 transmits an ultrasound signal to an object 10 according to a driving signal applied by the ultrasound transmission and reception unit 100 and receives an echo signal reflected from the object 10. The probe 20 includes a plurality of transducers. The plurality of transducers is vibrated according to electric signals provided to generate ultrasound waves that are waves of sound energy. The probe may be connected to a body of the ultrasound apparatus 1000 in a wired or wireless manner. The ultrasound apparatus 1000 may include a plurality of probes 20 depending on an implementation.

A transmission unit 110 supplies the driving signal to the probe 20 and includes a pulse generation unit 112, a transmission delay unit 114, and a pulser 116. The pulse generation unit 112 generates pulses for generating transmission ultrasound waves according to a predetermined pulse repetition frequency (PRF). The transmission delay unit 114 applies a delay time for determining transmission directionality to pulses. The respective pulses to which the delay time is applied respectively correspond to a plurality of piezoelectric vibrators included in the probe 20. The pulser 116 applies the driving signal (for example, a driving pulse) to the probe 20 with timings corresponding to the respective pulses to which the delay time is applied.

A reception unit 120 may generate ultrasound data by processing the echo signal received from the probe 20 and include an amplifier 122, an analog-digital converter (ADC) 124, a reception delay unit 126, and a summing unit 128. The amplifier 122 amplifies the echo signal for each channel. The ADC 124 performs analog-digital conversion on the amplified echo signal. The reception delay unit 126 applies a delay time for determining reception directionality to the digitally-converted echo signal. The summing unit 128 generates the ultrasound data by summing up the echo signals processed by the reception delay unit 126.

The image processing unit 200 generates an ultrasound image by performing scan conversion on the ultrasound data generated by the ultrasound transmission and reception unit 100 and displays the ultrasound image. The ultrasound image may be represented by not only a gray scale ultrasound image acquired by scanning an object according to an A mode, a B mode, or an M mode, but also a Doppler image showing movement of the object. The Doppler image may include a blood flow Doppler image (referred as a cooler Doppler image) showing a blood flow, a tissue Doppler image showing movement of tissue, and a spectral Doppler image showing a movement velocity of an object by using a waveform.

The B mode processing unit 212 extracts and processes a B mode component from the ultrasound data. The image generation unit 220 may generate an ultrasound image in which the intensity of a signal is represented by brightness based on the B mode component extracted by the B mode processing unit 212.

The Doppler processing unit 214 may extract a Doppler component from the ultrasound image. The image generation unit 220 may generate a Doppler image showing movement of an object as colors or waveforms based on the extracted Doppler component.

The image generation unit 220 may generate a three-dimensional ultrasound image by performing a volume rendering process on volume data and generate an elastic image in which the degree of deformation of the object 10 according to pressure is imaged. The image generation unit 220 may display various additional information on the ultrasound image in a graphical or text from. The generated ultrasound image may be stored in the memory 400.

The ultrasound apparatus 1000 may include two or more display units 1100 depending on an implementation.

The communication unit 300 is connected to a network 30 in a wired or wireless manner to communicate with an external device or server. The communication unit 300 may transmit and receive data to and from a hospital server connected thereto via a PACS or other medical apparatuses with in a hospital. The communication unit 300 may perform data communication according to a digital imaging and communications in medicine (DICOM) standard.

The communication unit 300 may transmit and receive data associated with diagnosis of an object, such as the ultrasound image of the object, ultrasound data, and the Doppler data through the network 30 and also transmit and receive a medical image captured by other medical apparatus, such as a CT imaging apparatus, a MRI imaging apparatus, and a X-ray imaging apparatus. The communication unit 300 may receive information on a diagnosis history and treatment schedule of a patient from the server to use the information to diagnose the patient. The communication unit 300 may perform data communication with a doctor's or a patient's portable terminal in addition to the server and the medical apparatus within the hospital.

The communication unit 300 may be connected to the network 30 in a wired or wireless manner to transmit and receive data to and from the server 32, the medical apparatus 34 or the portable terminal 36. The communication unit 300 may include one or more components that enable commutation with an external device, for example, a near filed communication module 310, a wired communication module 320, and a mobile communication module 330.

The near filed communication module 310 refers to a module for near field communication within a predetermined distance. Near filed communication technologies according to an exemplary embodiment may include a wireless LAN, a Wi-Fi, Bluetooth, a Wi-Fi direct (WFD), ultra wideband (UWB), infrared data association (IrDA), Bluetooth low energy (BLE), and a near filed communication (NFC), but is not limited thereto.

The wired communication module 320 refers to a module for communication using an electric signal or an optical signal. Wired communication technologies according to an exemplary embodiment may include a pair cable, a coaxial cable, an optical-fiber cable, and an Ethernet cable.

The mobile communication module 330 transmits and receives radio signals to and from at least one of a base station, an external terminal, and a server on a mobile communication network. The radio signals may include a voice call signal, a video call signal, or various types of data according to transmission and reception of short message service (SMS)/multimedia message service (MMS) messages.

The memory 400 stores various information processed in the ultrasound apparatus 1000. For example, the memory 400 may store medical data associated with diagnosis of an object, such as input/output ultrasound data and ultrasound images, and algorithms or programs executed by the ultrasound apparatus 1000. For example, the ultrasound apparatus 1000 may store information of interest to be measured, a method of determining a region of interest, and a method of measuring information of interest on the region of interest, corresponding to a measurement tool.

The memory 400 may be implemented by using various types of recoding mediums, such as a flash memory, a hard disk, and an EEPROM. The ultrasound apparatus 1000 may utilize a web storage server or a cloud server that performs a storage function of the memory 400 online.

The user input unit 1200 may further include various input units, such as an electrocardiogram (ECG) measurement module, a breath measurement module, a voice recognition sensor, a gesture recognition sensor, a fingerprint recognition sensor, a iris recognition sensor, a depth sensor, and a distance sensor.

All or some of the probe 20, the ultrasound transmission and reception unit 100, the image processing unit, the communication unit 300, the user input unit 1200, and the control unit may be implemented as software modules, but exemplary embodiments are not limited thereto. Some of the above-described configurations may be implemented as hardware. At least one of the ultrasound transmission and reception unit 100, the image processing unit 200, and the communication unit 300 may be included in the control unit 1300, but exemplary embodiments is not limited thereto.

In addition, other exemplary embodiments can also be implemented through computer readable code/instructions in/on a medium, e.g., a computer readable medium, to control at least one processing element to implement any above described exemplary embodiment. The medium can correspond to any medium/media permitting the storage and/or transmission of the computer readable code.

The computer readable code can be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as Internet transmission media. Thus, the medium may be such a defined and measurable structure including or carrying a signal or information, such as a device carrying a bitstream according to one or more exemplary embodiments. The media may also be a distributed network, so that the computer readable code is stored/transferred and executed in a distributed fashion. Furthermore, the processing element could include a processor or a computer processor, and processing elements may be distributed and/or included in a single device.

While one or more exemplary embodiments have been described with reference to the figures, it will be understood by those of ordinary skill in the art that various changes in form and details may be made therein without departing from the spirit and scope as defined by the following claims.

What is claimed is:

1. A method of measuring an ultrasound image in an ultrasound apparatus, comprising:
    displaying an ultrasound image on a screen;
    receiving, by a user input interface, a first user input of selecting at least two first coordinates on the ultrasound image;
    determining, based on a match of the first user input to a first one of stored user inputs in a memory of the ultrasound apparatus determined by a processor of the ultrasound apparatus, a first measurement tool;
    activating, by the processor, the first measurement tool corresponding to the first matched user input;
    acquiring first measurement information on the ultrasound image by using the first measurement tool;
    receiving, by the user input interface, a second user input of selecting at least one second coordinate on the ultrasound image;
    determining, based on a match of the second user input to a second one of the stored user inputs determined by the processor, a second measurement tool;
    switching from the first measurement tool corresponding to the first matched user input to the second measurement tool corresponding to the second matched user input, the second measurement tool being displayed on the ultrasound image; and
    acquiring second measurement information on the ultrasound image by using the second measurement tool,
    wherein the first measurement information and the second measurement information are different kinds of information.

2. The method of claim 1, wherein the first user input includes at least one of a click, a double click, and a click and drag.

3. The method of claim 1, wherein the determining of the first measurement tool comprises determining the first measurement tool in consideration of a type of the ultrasound image.

4. The method of claim 3, wherein the type of the ultrasound image includes at least one of a brightness (B) mode image, a motion (M) mode image, a spectral Doppler image, a color Doppler image, a tissue Doppler image, and an elastic Doppler image.

5. The method of claim 1, wherein the determining of the first measurement tool comprises:
    comparing a type of the first user input with preset input pattern information; and
    determining the first measurement tool based on a result of the comparing.

6. The method of claim 5, wherein the preset input pattern information includes at least one of input sequence information, input position information, click duration information, and drag direction information.

7. The method of claim 1, wherein the determining of the first measurement tool comprises:
    displaying a plurality of lines by using the at least two first coordinates as a reference according to the first user input; and
    determining the first measurement tool based on a number of intersection points between the plurality of lines, positions of an intersection points, and an intersection angle.

8. The method of claim 7, wherein the acquiring of the first measurement information on the ultrasound image comprises measuring at least one of lengths and slopes of the displayed plurality of lines.

9. The method of claim 7, wherein
    the plurality of lines includes a plurality of straight lines, and the acquiring of the first measurement information on the ultrasound image comprises measuring an intersection angle between the plurality of straight lines.

10. The method of claim 1, wherein the acquiring of the first measurement information on the ultrasound image comprises:
determining a region of interest based on the at least two first coordinates; and
measuring at least one of an area and circumference of the region of interest.

11. The method of claim 1, wherein the acquiring of the first measurement information on the ultrasound image comprises, when the ultrasound image is a spectral Doppler image, acquiring velocity information on the spectral Doppler image by using the first measurement tool.

12. The method of claim 1, wherein the acquiring of the first measurement information on the ultrasound image comprises:
when the ultrasound image is a spectral Doppler image, selecting a partial time interval on the spectral Doppler image based on the at least two first coordinates; and
measuring at least one of a distance which blood moves or a distance which tissue moves over the partial time interval and an envelope of a spectral waveform on the spectral Doppler image.

13. The method of claim 1, wherein the determining of the first measurement tool comprises determining a shape of a first region of interest corresponding to the first user input and determining first information of interest, and
the acquiring of the first measurement information by using the first measurement tool comprises:
determining a region of interest based on the determined shape of the first region of interest; and
measuring the determined first information of interest on the determined region of interest.

14. The method of claim 1, further comprising:
receiving a third user input of cancelling a previous user input of selecting a coordinate on the ultrasound image; and
switching from the second measurement tool to the first measurement tool according to the third user input, the first measurement tool being displayed on the ultrasound image.

15. The method of claim 1, further comprising:
receiving a fourth user input of cancelling all previous user inputs of selecting coordinates on the ultrasound image; and
cancelling the determination of the first measurement tool and determination of the second measurement tool, according to the fourth user input.

16. An ultrasound apparatus comprising:
a display unit configured to display an ultrasound image on a screen;
a user input interface configured to receive a first user input of selecting at least two first coordinates on the ultrasound image; and
a processor configured to:
determine, based on a match of the first user input to a first one of stored user inputs in a memory of the ultrasound apparatus, a first measurement tool,
activate the first measurement tool corresponding to the first matched user input,
acquire first measurement information on the ultrasound image by using the first measurement tool,
receive a second user input of selecting at least one second coordinate on the ultrasound image via the user input interface,
determine, based on a match of the second user input to a second one of the stored user inputs, a second measurement tool,
switch from the first measurement tool corresponding to the first matched user input to the second measurement tool corresponding to the second matched user input, the second measurement tool being displayed on the ultrasound image, and
acquire second measurement information on the ultrasound image by using the second measurement tool,
wherein the first measurement information and the second measurement information are different kinds of information.

17. The ultrasound apparatus of claim 16, wherein the first user input includes at least one of a click, a double click, and a click and drag.

18. The ultrasound apparatus of claim 16, wherein the processor is further configured to determine the first measurement tool in consideration of a type of the ultrasound image.

19. The ultrasound apparatus of claim 18, wherein the type of the ultrasound image includes at least one of a brightness (B) mode image, a motion (M) mode image, a spectral Doppler image, a color Doppler image, a tissue Doppler image, and an elastic Doppler image.

20. The ultrasound apparatus of claim 16, wherein the processor is further configured to:
compare a type of the first user input with preset input pattern information, and
determine the first measurement tool based on a result of the comparing.

21. The ultrasound apparatus of claim 20, wherein the preset input pattern information includes at least one of input sequence information, input position information, click duration information, and drag direction information.

22. The ultrasound apparatus of claim 16, wherein the processor is further configured to:
display a plurality of lines by using the at least two first coordinates as a reference according to the first user input, and
determine the first measurement tool based on a number of intersection points between the plurality of lines, positions of the intersection points, and an intersection angle.

23. The ultrasound apparatus of claim 22, wherein the processor is further configured to measure at least one of lengths and slopes of the displayed plurality of lines.

24. The ultrasound apparatus of claim 22, wherein
the plurality of lines includes a plurality of straight lines, and
the processor is further configured to measure an intersection angle between the plurality of lines.

25. The ultrasound apparatus of claim 16, wherein the processor is further configured to:
determine a region of interest based on at least two first coordinates, and
measure at least one of an area and circumference of the region of interest.

26. The ultrasound apparatus of claim 16, wherein the processor is further configured to acquire, when the ultrasound image is a spectral Doppler image, velocity information on the spectral Doppler image by using the first measurement tool.

27. The ultrasound apparatus of claim 16, wherein the processor is further configured to:
- select, when the ultrasound image is a spectral Doppler image, a partial time interval on the spectral Doppler image based on the at least two first coordinates, and
- measure at least one of a distance which blood moves or a distance which tissue moves over the partial time interval and an envelope of a spectral waveform on the spectral Doppler image.

28. The ultrasound apparatus of claim 16, wherein the processor is further configured to:
- determine a shape of a first region of interest corresponding to the first user input and determine first information of interest,
- determine a region of interest based on the determined shape of the first region of interest, and
- measure the first information of interest on the determined region of interest.

29. The ultrasound apparatus of claim 16, wherein
- the user input interface is further configured to receive a third user input of cancelling a previous user input of selecting a coordinate on the ultrasound image, and
- the processor is further configured to switch from the second measurement tool to the first measurement tool according to the third user input, the first measurement tool being displayed on the ultrasound image.

30. The ultrasound apparatus of claim 16, wherein
- the user input interface is further configured to receive a fourth user input of cancelling all previous user inputs of selecting coordinates on the ultrasound image, and
- the processor is further configured to cancel the determination of the first measurement tool and determination of the second measurement tool, according to the fourth user input.

31. A non-transitory computer-readable recording medium storing a program which, when executed by a computer, performs the method of claim 1.

* * * * *